United States Patent [19]

Lamanna et al.

[11] Patent Number: 5,514,728
[45] Date of Patent: May 7, 1996

[54] CATALYSTS AND INITIATORS FOR POLYMERIZATION

[75] Inventors: William M. Lamanna, Stillwater; Michael C. Palazzotto, St. Paul; Robert J. DeVoe, Oakdale; Fred B. McCormick, Maplewood; Jeffrey M. Olofson, Woodbury; Allen R. Siedle, Lake Elmo; Peggy S. Willett, Stillwater, all of Minn.

[73] Assignee: Minnesota Mining and Manufacturing Company, St. Paul, Minn.

[21] Appl. No.: 97,279

[22] Filed: Jul. 23, 1993

[51] Int. Cl.$^6$ .................................. C08F 2/46; C08F 4/06
[52] U.S. Cl. .................. 522/31; 522/49; 522/65; 522/66; 526/89; 526/131; 526/195
[58] Field of Search ........................... 522/31, 49, 65, 522/66; 526/89, 131, 195

[56] References Cited

U.S. PATENT DOCUMENTS

| | | | |
|---|---|---|---|
| 3,542,828 | 11/1970 | Harris | 260/446 |
| 3,586,616 | 6/1971 | Kropp | 204/159.11 |
| 3,708,296 | 1/1972 | Sheldon | 96/33 |
| 3,907,706 | 9/1975 | Robins | 252/431 |
| 3,998,763 | 12/1976 | Bohnel | 260/2 EC |
| 4,058,401 | 11/1977 | Crivello | 96/115 |
| 4,069,055 | 1/1978 | Crivello | 96/115 R |
| 4,216,288 | 8/1980 | Crivello | 430/280 |
| 4,250,311 | 2/1981 | Crivello | 546/9 |
| 4,264,703 | 4/1981 | Crivello | 430/270 |
| 4,340,716 | 7/1982 | Hata et al. | 528/100 |
| 4,503,211 | 3/1985 | Robins | 528/92 |
| 4,677,137 | 6/1987 | Bony et al. | 522/31 |
| 4,868,288 | 9/1989 | Meier | 534/15 |
| 4,954,414 | 9/1990 | Adair et al. | 430/138 |
| 4,954,616 | 9/1990 | Callens et al. | 530/333 |
| 4,985,340 | 1/1991 | Palazzotto et al. | 430/270 |
| 5,011,760 | 4/1991 | Yamaguchi et al. | 430/281 |
| 5,059,701 | 10/1991 | Keipert | 556/13 |
| 5,073,476 | 12/1991 | Meier et al. | 430/280 |
| 5,084,586 | 1/1992 | Farooq | 556/181 |
| 5,124,417 | 6/1992 | Farooq | 526/90 |
| 5,143,785 | 9/1992 | Pujol et al. | 428/352 |
| 5,215,860 | 6/1993 | McCormick et al. | 430/270 |

FOREIGN PATENT DOCUMENTS

| | | | |
|---|---|---|---|
| 35170 | 9/1993 | Australia | C07F 17/00 |
| 0094914B1 | 11/1983 | European Pat. Off. | G03C 1/68 |
| 109851A2 | 5/1984 | European Pat. Off. | C08F 4/72 |
| 0353030 | 1/1990 | European Pat. Off. | C07F 5/02 |
| 0412430A2 | 2/1991 | European Pat. Off. | C07F 7/21 |
| 0418044A2 | 3/1991 | European Pat. Off. | C08F 10/00 |
| 0421659A2 | 4/1991 | European Pat. Off. | C08F 12/00 |
| 0426637A2 | 5/1991 | European Pat. Off. | C08F 4/603 |
| 0442635A1 | 8/1991 | European Pat. Off. | C07F 19/00 |
| 0447115A1 | 9/1991 | European Pat. Off. | C09D 4/06 |
| 0454231A2 | 10/1991 | European Pat. Off. | C08F 4/70 |
| 0468651A1 | 1/1992 | European Pat. Off. | C08F 4/74 |
| 0562897A1 | 9/1993 | European Pat. Off. | C07F 5/02 |
| 0562922A1 | 9/1993 | European Pat. Off. | C09D 183/06 |
| 963058 | 7/1964 | United Kingdom . | |
| 1495746 | 12/1977 | United Kingdom | C08F 22/38 |
| WO88/05793 | 8/1988 | WIPO | C08F 4/64 |

OTHER PUBLICATIONS

Murov, "Handbook of Photochemistry", Marcel Dekker Inc. pp. 27–35 (1973).
D. R. McKean et al., "Polymeric Materials Sci. Eng." vol. 61, pp. 81–85 (1989).
Yang et al., "Organometallics", vol. 10, pp. 840–842 (1991).
Kobayashi et al., "Kenkyu Hococu—Asahi Garasu Kogyo Gijutsu Shoreikai" vol. 42, pp. 137–145 (1983) Abstracts, Figures, and Tables are in English.
Ichikawa et al., "Anionic Phase–Transfer Catalysis with TFPB Ion", pp. 943–954 Abstracts, Figures and Tables are in English—1984.
Borden, "Photographic Science and Engineering", vol. 16, No. 4, pp. 300–312 (Jul./Aug. 1972).
J. Am. Chem. Soc. 111, pp. 6070–6081 (1989).
J. Am. Chem. Soc., 113, pp. 8570–8571 (1991).
Horowitz et al., "The Anodic Oxidation Stability of Lithium Electrolytes", pp. 131–143, 1983.
Dietliker, "Chemistry & Technology of UV & EB Formulation for Coatings, Inks and Paints", vol. 3, pp. 433–434 (1991).
J. Am. Chem. Soc., 113, pp. 3623–3625 (1991).
Crivello, "Polymers In Electronics", pp. 3–10 (1984).
Nagamura et al. Ber. Bunsenges, Phys. Chem. 93, pp. 1432–1436 (1989).
Crivello et al., "Chem. Mater. 1992", 4, 692–699.
Massey et al., "Tris(pentafluorophenyl)boron and Its Adducts" pp. 461–463—1980.
Nishida et al., "Bull. Chem. Soc. Jpn.", 57, No. 9, pp. 2600–2604 (1984).
J. Am. Chem. Soc. 113, pp. 2777–2779 (1991).
Brookhart et al., "Polymer Preprints", vol. 32, No. 1, pp. 461 & 462 (1991).
Iwamoto, "Tetrahedron Letters", vol. 24, No. 32, pp. 4703–4706 (1983).
Iwamoto et al., "Bull. Chem. Soc. Jpn.", vol. 56, No. 3, pp. 796–801 (1983).
Kobayashi et al., "Chemistry Letters", pp. 579–580 (1981).
Nishida et al., "Bull. Chem. Soc. Jpn.", vol. 57, No. 9, pp. 2600–2604 (1984).
Journal of Polymer Science: Polymer Letters Edition, vol. 17, 759–764 (1979).

(List continued on next page.)

*Primary Examiner*—Mark Chapman
*Attorney, Agent, or Firm*—Gary L. Griswold; Walter N. Kirn; Carolyn V. Peters

[57] ABSTRACT

Salts having a cationic portion of either a mono-, polyvent metal center, onium salts or organometallic salts and a nonnucleophilic anion are useful as catalysts and initiators that may be photochemically or thermally-activated, and polymerizable compositions containing such catalysts and initiator salts and at least one of a cationic or free-radical addition polymerizable monomers, or catalyzed step-growth polymerizable monomers.

15 Claims, No Drawings

OTHER PUBLICATIONS

Journal of Organometallic Chemistry, 424 (1992) C5–C7.
"American Chemical Society", Inorg. Chem. 1991, 30, pp. 4687–4690.
Nagamura et al. "J. Chem. Soc.", Faraday Trans. 1, 84(10), pp. 3529–3537 (1988).
J. Chem. Soc., "Chem. Commun." pp. 72–74 (1991).
Nagamura et al., "Ber. Bunsenges. Phys. Chem. 92", pp. 707–710 (1988).
H. F. Mark et al., "Encyclopedia of Polymer Science and Engineering" 2nd Ed. pp. 729–814 (1985).
Paulson et al., "J. Che. Soc." Dalton Trans., pp. 1677 & 1683 (1975).
"Chemistry Letters", pp. 1185 & 1186 (1982).
F. A. Cotton et al., "Basic Inorganic Chemistry", Chapter 29, pp. 497–527 (1976).
Brookhart et al., "Organometallics", vol. 2, No. 5, pp. 638–649 (1983).

CATALYSTS AND INITIATORS FOR POLYMERIZATION

TECHNICAL FIELD

This invention relates to salts of non-nucleophilic anions, and particularly to the use of the salts of non-nucleophilic anions as curing agents for thermally or photochemically induced cationic or free radical addition polymerization or catalyzed, step-growth polymerization and to a process for providing the polymerized composition of the invention is disclosed.

BACKGROUND OF THE INVENTION

Salts comprising an organic, inorganic or organometallic cation and a nonnucleophilic counteranion have been shown to have utility as photochemically and thermally activated initiators for cationic addition polymerization or as similarly activated latent catalysts for step-growth (or condensation) polymerization, depolymerization and unblocking of functionalized polymers. Common commercial photoinitiator salts include onium and organometallic salts such as diaryliodonium and triarylsulfonium salts and (cyclopentadienyl)(arene)iron$^+$ salts of the anions $PF_6^-$ and $SbF_6^-$. In certain cases, these same salts may also photoinitiate free-radical addition polymerization and are useful in "dual cure" applications where a mixture of cationically sensitive and free-radically polymerizable monomers are polymerized either simultaneously or sequentially.

For many commercial applications, the polymerizable monomers are multifunctional (i.e., contain more than one polymerizable group per molecule), for example, epoxides, such as diglycidyl ether of bisphenol A (DGEBA) and vinyl ethers, such as 1,4-cyclohexanedimethanol divinyl ether (CHVE). Mixtures of multifunctional monomers such as isocyanates and alcohols or epoxides and alcohols can undergo catalyzed polycondensation via a step-growth mechanism.

Photochemically activated initiators (or catalysts) typically provide homogeneous mixing of the monomers with the initiator prior to polymerization, or selective activation by light for imaging applications, such as photolithography. Simple photoinitiators typically have low absorption coefficients above 300 nm where a major portion of the spectral output of conventional light sources (i.e., medium and high pressure mercury lamps, fluorescent lamps or the sun) occurs. These low absorption coefficients tend to limit their photoefficiency.

To overcome this problem, a number of methods have been developed to improve the wavelength response of such photoinitiators. For example, photosensitizers may be added in combination with the photoinitiators to more efficiently transfer light energy to the cationic portion of the initiator. In addition synthetic modifications of the cationic portions of onium or organometallic photoinitiator salts can improve photoefficiency.

Synthetic modifications of the cationic portion have been made to improve the solubility of cationic photoinitiators, which, because of their ionic nature, tend to exhibit poor solubility in organic monomers. However, the difficulty and cost of introducing solubilizing substituents has limited commercial application of these materials. Alternative solutions that use reactive diluents or solid dispersants have also been disclosed.

In many applications photoinduced polymerization is impossible, impractical or undesirable. For example, in the many situations where the polymerization reaction occurs in a closed environment (i.e., in a mold or in a laminated product) or where the polymerizable composition may contain opacifying pigments, thermally activated initiators are preferred. The thermally-activated initiators, such as art known onium or organometallic salts may initiate polymerization at ambient or higher temperatures depending upon the specific application. Additional additives, such as oxidants, reductants, metal salts, organic acids or anhydrides, and mixtures thereof are frequently added to control the temperature at which cationic polymerization will occur.

In addition to the art known onium or organometallic salts, acid salts of various amines, metal salts of fluoroalkanesulfonic acids and bis(fluoroalkylsulfonyl)methanes have been used as thermal initiators for cationic addition polymerization of vinyl ethers and epoxies or catalysts for alcohol-epoxy step-growth polymerization.

A key feature of initiators for cationic addition polymerization is the ability to produce powerful Brönsted or Lewis acids upon thermal or photochemical activation. In order to achieve this, counteranions which are nonbasic, nonnucleophilic and nonreducing and therefore stable in a highly acidic and oxidizing environment are essential to prevent initiator deactivation or cationic chain termination. For this reason most cationic initiators used in cationic addition polymerization are based on the anions $SbF_6^-$, $AsF_6^-$, $PF_6^-$, and $BF_4^-$.

It is known the nature of the counteranion in a complex salt can influence the rate and extent of cationic addition polymerization. See for example, J. V. Crivello, R. Narayan, Chem. Mater., 4, 692, (1992), discussing the order of reactivity among commonly used nonnucleophilic anions is $SbF_6^- > AsF_6^- > PF_6^- > BF_4^-$. The influence of the anion on reactivity has been ascribed to three principle factors: 1) the strength of the protonic or Lewis acid generated, 2) the degree of ion-pair separation in the propagating cationic chain and 3) the susceptibility of the anions to fluoride abstraction and consequent chain termination. Evidence indicates that, for onium salts, the choice of anion has no effect on the photoefficiency of active acid production.

The use of tetrakis[3,5-bis(trifluoromethyl)phenyl]borate (TFPB$^-$) and related F- or CF$_3$-substituted tetraphenyl borates as highly lipophilic and chemically stable, anions for the extraction of alkali metal cations into organic solvents is described by H. Kobayashi, et. al. in Bull. Chem. Soc. Jpn., 57, 2600 (1984) and Kenkyu Hokoku-Asahi Garasu Kogyo Gijutsu Shoreikai, 42, 137–45, (1983). The further utility of Na[TFPB] anion as a phase transfer catalyst to promote electrophilic reactions (e.g. diazo coupling, Friedel-Crafts alkylation, nitrosation) in two phase, aqueous-organic systems is disclosed by H. Kobayashi, et. al. in Yuki Gosei Kagaku Kyokaishi, 46 (10), 943–54 (1988); Chemistry Letters, 579–580, 1981; ibid, 1185–6 (1982); Bull. Chem. Soc. Jpn., 56, 796–801 (1983) and Tetrahedron Lett., 24 (32), 4703–6 (1983). The accelerating or catalytic effect of TFPB$^-$ in these cases has been attributed to the "dehydration" (removal of solvated water) of the reactive cationic species upon transport into the nonpolar organic phase.

Photochromic salts of 4,4'-bipyridinium ions with TFPB$^-$ counteranion which undergo persistent and reversible color changes due to photoinduced electron transfer upon excitation of an ion-pair charge-transfer band have been described by T. Nagamura, et al. in Ber. Bunsen-Ges. Phys. Chem., 93 (12), 1432–6 (1989); ibid, 92 (6), 707–10 (1988); J. Chem.

Soc. Chem. Commun., 72–74, (1991) and J. Chem. Soc., Faraday Trans. 1, 84 (10), 3529–37, (1988).

K. R. Mann, W. M. Lamanna and M. G. Hill in Inorg. Chem., 30, 4687 (1991) describe the use of tetrabutylammonium [TFPB] as a convenient noncoordinating electrolyte for electrochemical studies in methylene chloride solution.

M. Brookhart, et. al., Polymer Preprints, 32 (1), 461 (1991) and U.S. patent application No. 07/513,241 filed Apr. 20, 1990 describes TFPB$^-$ salts of organometallic metalalkyl or metal-hydride cations which are useful catalysts for Ziegler-Natta type polymerization of ethylene and higher olefins. The TFPB$^-$ anion provides improved catalyst stability relative to analogous $BF_4^-$ salts. In related work, M. Brookhart, S. Sabo-Etienne, J. Am. Chem. Soc., 113, 2777–79 (1991) describes a TFPB$^-$ salt of an organometallic rhodium-hydride cation, which is an efficient catalyst for the tail-to-tail dimerization of methyl acrylate.

M. Bochmann, A. J. Jaggar, J. Organometal. Chem., 424, C5–7 (1992) describes cationic titanium-alkyl salts of TFPB$^-$ which are active catalysts for the Ziegler-Natta type polymerization of ethylene. The TFPB$^-$ anion provides improved catalyst activity and solubility compared to simple tetraphenylborate. Other cationic metal-alkyl catalysts have been described which utilize fluorine substituted aryl borate counteranions, most notably $(C_6F_5)_4B^-$, $(CH_3)(C_6F_5)_3B^-$. The catalysts are useful for the Ziegler-Natta polymerization of hydrocarbon olefins such as ethylene and propylene.

J. V. Crivello, J. H. W. Lam, J. Polym. Sci., Polym. Lett. Ed., 17(12), 759 (1979), describe the reactivity of triphenylsulfonium tetraphenylborate as a photoinitiator. Although active for free-radical polymerization, the tetraphenylborate salt was found to be completely inactive for cationic addition polymerization of cyclohexene oxide, a particularly reactive epoxy monomer. The absence of epoxy reactivity contrasts with the high level of epoxy-curing activity displayed by the corresponding triphenylsulfonium [SbF$_6$] salt. The difference is attributed to the relatively nucleophilic or basic character of the tetraphenylborate anion.

SUMMARY OF THE INVENTION

In one aspect of the present invention, an initiator salt is provided having a cationic portion and an anionic portion wherein the anionic portion of the salt is a nonnucleophilic anion (also referred to as "nonnucleophilic salts") and has the formula:

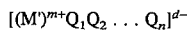

wherein:
M' is a metal or metalloid selected from the groups subtended by Groups IVB to VA of the Periodic Table of the Elements (CAS Version); i.e., Groups IVB, VB, VIB, VIIB, VIII, IB, IIB, IIIA, IVA, and VA, preferably Groups IIIA and VA, most preferably Group IIIA;
$Q_1$ to $Q_n$ are selected, independently from the group consisting of halide radicals, dialkylamido radicals, hydroxide, alkoxide and aryloxide radicals, hydrocarbyl-mercaptide and-carboxylate radicals, hydrocarbyl and substituted hydrocarbyl radicals, and organometalloid radicals, where at least one of $Q_1$ to $Q_n$ is a halogen-substituted aromatic hydrocarbyl radical, but not more than (n–1) of $Q_1$ to $Q_n$ may be a halide radical, with the remaining $Q_1$ to $Q_n$ being selected from the foregoing radicals;
m is an integer from 1 to 6;
n is an integer from 2 to 7; and
(n–m)=d.

In a preferred embodiment, M' is boron, n is 4, $Q_1$ is a substituted aromatic group (Ar), and $Q_2$ to $Q_4$ are as described above and the nonnucleophilic anion has the formula:

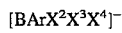

wherein:
B is boron in a valence state of 3;
Ar is a halogen substituted aromatic hydrocarbon radical containing from about 6 to about 30 carbon atoms and may be linked to one or more X groups through a stable bridging group; and
$X^2$, $X^3$ and $X^4$ are radicals selected, independently, from the group consisting of halide radicals, hydrocarbyl radicals containing from 1 to about 30 carbon atoms, substituted hydrocarbyl radicals containing 1 to about 30 carbon atoms, wherein one or more of the hydrogen atoms is replaced by a halogen atom, dialkylamido radicals, hydroxide, alkoxide and aryloxide radicals, hydrocarbyl-mercaptide and -carboxylate radicals, wherein the alkyl and aryl hydrocarbyl portions of the radicals contain from 1 to about 30 carbon atoms, and hydrocarbon substituted metal (organometalloid) radicals, wherein each hydrocarbyl substitution contains from 1 to about 20 carbon atoms and the metal is selected from Group IVA of the Periodic Table of the Elements.

The cationic portion of the initiator salts can be selected from the group consisting of mono or polyvalent metal cations having a valence of 1–5; organic onium salts, such as iodonium, or sulfonium salts; and organometallic complex cations.

In another aspect, this invention relates to a polymerizable composition comprising (a) at least one of a cationic addition polymerizable monomer, a free radically polymerizable ethylenically-unsaturated monomer, or a catalyzed step-growth polymerizable monomer and, (b) at least one nonnucleophilic salt according to the above formula. The polymerized compositions are useful, for example, as protective coatings, release liners, adhesives, abrasive binders and in graphic arts and photoresist applications.

Advantageously, the nonnucleophilic salts of the present invention provide improved solubility. In many cases photosensitivity and wavelength response is improved. Further, a particular class of the nonnucleophilic salts of the present invention exhibit improved thermal stability over analogous art known SbF$_6^-$ salts. Further advantages of the present invention include improved polymerization yield, cure speed, low toxicity, control of the onset and rate of polymerization, and corrosion resistance, that is, low HF liberation.

As used in this application:
"catalytically effective amount" means a quantity sufficient to effect polymerization of the curable composition to a polymerized product at least to a degree to cause an increase in viscosity of the composition under the conditions specified;

"monomer" and "ligand" means a chemical species that allows for substitution or which may be substituted by conventional substituents, in addition to what may described and that do not interfere with the desired product, e.g., subitituents can be alkyl, alkoxy, aryl, phenyl, aryalkoxy, hydroxyl, cyano, carboxyl, amino, nitro, acetyl, halo (F, Cl, Br, I), etc;

"organometallic salt" means an ionic salt of an organometallic complex cation, wherein the cation contains at least one carbon atom of an organic group that is bonded to a metal atom of a transition metal series (F. A. Cotton, G. Wilkinson *Basic Inorganic Chemistry*, Wiley, 1976, p. 497);

"polymerizable composition" means a mixture of an initiator or catalyst and polymerizable monomer(s); and "polymerize" and "cure" are interchangeable and mean to supply sufficient energy to a composition to alter the physical state of the composition, to make it transform from a fluid to less fluid state, to go from a tacky or non-tacky state, to go from a soluble to insoluble state, or to decrease the amount of polymerizable monomer by its consumption in a reaction.

DESCRIPTION OF THE PREFERRED EMBODIMENT(S)

The present invention provides catalysts and initiators that may be photochemically or thermally-activated, and polymerizable compositions containing such catalysts and initiators. Nonnucleophilic salts as catalysts and initiators are particularly useful for cationic, and free-radical addition polymerization and catalyzed step-growth polymerizations.

The polymerizable compositions comprise mixtures of at least one of aforementioned catalysts or initiators with (1) at least one monomer polymerizable by cationic addition polymerization, or (2) at least one monomer polymerizable by catalyzed step-growth polymerization, or (3) at least one ethylenically unsaturated monomer polymerizable by free-radical addition polymerization or (4) mixtures containing any combination of the various classes of monomers described above.

The catalysts and initiators are salts comprised of (1) a thermally or photochemically reactive cationic portion, which serves as the latent source of Brönsted or Lewis acid (and, optionally, free radicals) necessary to initiate or catalyze polymerization and (2) a nonnucleophilic counteranion.

Non-nucleophilic Anions

Non-nucleophilic anions useful as counteranions in the preparation of initiators or catalysts useful in practicing the present invention comprise a single coordination complex possessing a negative charge bearing metal or metalloid core, which anion is relatively large (bulky), nonbasic, nonreactive and either noncoordinating or only weakly coordinating towards and compatible with the cationic portion of the initiator or the propagating cationic center of a growing cationic addition polymer chain or other cationic species, such as Brönsted or Lewis acid species, involved in the catalyzed or initiated polymerization.

In general, nonnucleophilic anions useful in the preparation of initiators or catalysts of this invention may be represented by the following formula:

$$[(M')^{m+}Q_1Q_2 \ldots Q_n]^{d-} \qquad (1)$$

wherein:

M' is a metal or metalloid selected from the groups subtended by Groups IVB to VA of the Periodic Table of the Elements (CAS Version); i.e., Groups IVB, VB, VIB, VIIB, VIII, IB, IIB, IIIA, IVA, and VA, preferably Groups IIIA and VA, most preferably Group IIIA.

$Q_1$ to $Q_n$ are selected, independently from the group consisting of halide radicals, dialkylamido radicals; hydroxide, alkoxide and aryloxide radicals; hydrocarbyl-mercaptide and -carboxylate radicals; hydrocarbyl and substituted hydrocarbyl radicals; and organometalloid radicals, where at least one of $Q_1$ to $Q_n$ is a halogen-substituted aromatic hydrocarbyl radical, but not more than (n−1) of $Q_1$ to $Q_n$ may be a halide radical, with the remaining $Q_1$ to $Q_n$ being selected from the foregoing radicals;

m is an integer from 1 to 6;
n is an integer from 2 to 7; and
(n−m)=d.

Boron-centered anions are particularly useful in the preparation of initiators or catalysts useful in the present invention and may be represented by the following formula:

$$[BArX^2X^3X^4]^- \qquad (2)$$

wherein:

B is boron in a valence state of 3;

Ar is a halogen-substituted aromatic hydrocarbon radical containing from about 6 to about 30 carbon atoms and may be linked to one or more X groups through one or more stable bridging groups; and $X^2$, $X^3$ and $X^4$ are radicals each independently selected from the group consisting of halide radicals; hydrocarbyl radicals containing from 1 to about 30 carbon atoms; substituted hydrocarbyl radicals containing 1 to about 30 carbon atoms, wherein one or more of the hydrogen atoms is replaced by a halogen atom; dialkylamido radicals; hydroxide, alkoxide and aryloxide radicals; hydrocarbylmercaptide and -carboxylate radicals, wherein the alkyl and aryl hydrocarbyl portions of the radicals contain from 1 to about 30 carbon atoms; and hydrocarbon-substituted metal (organometalloid) radicals, wherein each hydrocarbyl substitution contains from 1 to about 20 carbon atoms and the metal is selected from Group IVA of the Periodic Table of the Elements.

Useful stable bridging groups include a single bond, a double bond, $-\!(\!(CH_2)_n\!)\!-$ where n is 1 to 4; $-\!(\!(CF_2)_m\!)\!-$ where m is 1 to 4; $-\!(\!(CH)_2\!)\!-$; $(R)_2Si=\!\!=$; $(R)_2C=\!\!=$; $(R)_2Sn=\!\!=$; $(R)_2Ge=\!\!=$; O; S; Se; $=\!\!CO$; $=\!\!SO_2$; $RN=\!\!=$; or $RP=\!\!=$, where R is substituted or unsubstituted aryl or alkyl hydrocarbyl group.

In general, Ar may be any halogen-substituted aromatic hydrocarbon radical containing from about 6 to about 30 carbon atoms. Suitable aromatic radicals include, but are not limited to, phenyl, naphthyl and anthracenyl radicals. Preferred halogen substituents include chlorine and fluorine, and more preferably fluorine. Halogen substituents of the aromatic hydrocarbon may be halogen radicals bound directly to the aromatic ring or may be incorporated as part of another substituent group as in the case of halo-hydrocarbyl radical substituents, wherein fluoro-hydrocarbyl substituents are preferred. Other suitable substituents on useful halogen-substituted aromatic hydrocarbon radicals include, but are not necessarily limited to hydrocarbyl radicals, organometalloid radicals, and the like such as those useful as $X^2$, $X^3$ and $X^4$. The substituents may be ortho, meta or para, relative to the carbon atom bonded to the boron atom. When any or all of $X^2$, $X^3$ and $X^4$ are a halogen substituted hydrocarbyl radical, each may be the same or a different halogen substituted aromatic hydrocarbon radical as Ar.

Illustrative, but not limiting, examples of boron-centered anions useful in the initiators or catalysts of this invention are:

$[3,5\text{-}(CF_3)_2C_6H_3]_4B^-$ $(C_6F_5)_4B^-$ $(C_6H_4\text{—}p\text{—}CF_3)_4B^-$ $(C_6H_4\text{—}m\text{—}CF_3)_4B^-$ $(C_6H_4\text{—}p\text{—}F)_4B^-$ $(C_6F_5)_3(CH_3)B^-$ $(C_6F_5)_3(n\text{—}C_4H_9)B^-$ $(C_6H_4-p-CH_3)_3(C_6F_5)B^-$ $(C_6F_5)_3FB^-$ $(C_6H_5)_3(C_6F_5)B^-$ $(CH_3)_2(C_6H_4-p-CF_3)_2B^-$ $(C_6F_5)_3(n-C_{18}H_{37}O)B^-$ Preferred boron-centered anions of this invention generally contain 3 or more halogen-substituted aromatic hydrocarbon radicals attached to boron where the halogen is most preferably fluorine. Illustrative, but not limiting, examples of the most preferred anions are $[3,5-(CF_3)_2C_6H_3]_4B^-$, $(C_6F_5)_4B^-$, $(C_6F_5)_3(n-C_4H_9)B^-$, $(C_6F_5)_3FB^-$ and $(C_6F_5)_3(CH_3)B^-$.

Similar lists of suitable anions containing other metal or metalloid centers, which are useful could be made, and include, for example $[3,5-(CF_3)_2C_6H_3]_4Al^-$, $(C_6F_5)_4Al^-$, $(C_6F_5)_2F_4P^-$, $(C_6F_5)F_5Sb^-$ and $(C_6F_5)F_5P^-$. In this regard, it should be noted that the foregoing lists are not intended to be exhaustive and other boron-centered nonnucleophilic salts that would be useful, as well as other useful anions containing other metals or metalloids, would be readily apparent, from the foregoing general formulas, to those skilled in the art.

Cations

Classes of cations useful as the cationic portion of the catalysts and initiators of this invention include (1) mono- or polyvalent metal cations preferably having a valence of 1–5 selected from the group consisting of metals of Groups IA–IIIA, IB–VIIB, VIII and those of the lanthanide and actinide series of the Periodic Table of the Elements (CAS Version);

(2) organic onium cations, for example those described in U.S. Pat. Nos. 4,250,311, 3,708,296, 4,069,055, 4,216,288, 5,084,586 and 5,124,417 and such descriptions incorporated herein by reference, including aliphatic or aromatic Group IVA–VIIA (CAS version) centered onium salts and preferably selected from diazonium, sulfoxonium, diaryliodonium, triarylsulfonium, and protonated aliphatic, aromatic or heterocyclic amines; or (3) organometallic complex cations essentially free of metal hydride or metal alkyl functionality selected from those described in U.S. Pat. No. 4,985,340 and such description is incorporated herein by reference and has the formula:

$$[(L^1)(L^2)M]^{+q}X_n \qquad (3)$$

wherein

M represents a metal selected from the group consisting of Cr, Mo, W, Mn Re, Fe, Ru, Os, Co, Rh, Ir, Pd, Pt and Ni;

$L^1$ represents 1 or 2 cyclic, polyunsaturated ligands that can be the same or different ligand selected from the group consisting of substituted and unsubstituted cyclopentadienyl, cyclohexadienyl, and cycloheptatrienyl, cycloheptatriene, cyclooctatetraene, heterocyclic compounds and aromatic compounds selected from substituted or unsubstituted benzene compounds and compounds having 2 to 4 fused rings, each capable of contributing 3 to 8 electrons to the valence shell of M;

$L^2$ represents none, or 1 to 3 nonanionic ligands contributing an even number of electrons that can be the same or different ligand selected from the group of carbon monoxide, ketones, olefins, ethers, nitrosonium, phosphines, phosphites, and related derivatives of arsenic and antimony organonitriles, amines, alkynes, isonitriles, dinitrogen, with the proviso that the total electronic charge contributed to M results in a net residual positive charge of q to the complex;

q is an integer having a value of 1 or 2, the residual charge of the complex cation;

X is the non-nucleophilic anion according to formula 1;

n is an integer having a value of 1 or 2, the number of complex anions required to neutralize the charge q on the complex cation;

Organometallic salts are known in the art and can be prepared as described in, for example, EPO Nos. 109,851, 094,914, 094,915 and 126,712, and such descriptions are incorporated herein by reference. The organometallic cations useful in the present invention are generally not useful for catalyzing Zeigler-Natta type polymerizations of olefins because such polymerization requires metal hydride or metal-alkyl functionality not present in the catalyst or initiator salts useful in the present invention. Furthermore, useful organometallic cations of the present invention do not require metal hydride or metal alkyl co-catalysts.

Nonnucleophilic salts of the above described anions and cations may be activated by radiation or by heat or may require two stage activation involving radiation followed by heat. Suitable salts having such cations and a nonnucleophilic anion for use in the polymerizable compositions of the instant invention are those salts that upon application of sufficient energy, thermal, accelerated particle (electron beam), or electromagnetic radiation having a wavelength from about 200 to 800 nm will generate an active species capable of initiating or catalyzing the polymerization of the polymerizable compositions of the invention. The level of catalyst or initiator activity will of course depend on the choice of cation and nonnucleophilic anion in the salt and on the monomer.

Salts of Non-nucleophilic Anions

Nonlimiting examples of catalysts and initiator salts of nonnucleophilic anions useful in the composition of the invention include the following:

(1) Metal Salts

Examples of metal salts include but are not limited to: $Li[B(C_6F_5)_4]$, $Ag[B(C_6F_5)_4]$, $Na[B(C_6F_5)_4]$, $Mg[[B(C_6F_5)_4]_2]$, $Li[B[3,5-(CF_3)_2C_6H_3]_4]$, $Na[B[3,5-(CF_3)_2C_6H_3]_4]$, $Zn[(B[3,5-(CF_3)_2C_6H_3]_4)_2]$, $Mg[(B[3,5-(CF_3)_2C_6H_4]_4)_2]$, $Na[B(CH_3)(C_6F_5)_3]$, $Ag[B(C_6F_5)_4][3\ toluene]$ and $Li[B(n-butyl)(C_6F_5)_3]$. The cationic portion of the metal salts may further be solvated with water or various organic solvents, such as ethers, amines, arenes, or ketones without departing from the scope of the present invention.

(2) Onium Salts

Examples of onium salts include but are not limited to: $(C_6H_5)_2I[B(C_6F_5)_4]$, $(CH_3C_6H_4)_2I[B(C_6F_5)_4]$, $(C_6H_5)_3S[B(C_6F_5)_4]$, $(C_6H_5)_3C[B(C_6F_5)_4]$, $(C_6H_5)_3S[BF(C_6F_5)_3]$, $(C_2H_5)_3NH[BF(C_6F_5)_3]$, $(C_2H_5)_2OH[B(C_6F_5)_4]$, $(C_2H_5)_3NH[B(C_6F_5)_4]$, $(C_6H_5)_2I[B[3,5-(CF_3)_2C_6H_3]_4]$, $(C_6H_5)_3S[B[3,5-(CF_3)_2C_6H_3]_4]$, $(C_2H_5)_2OH[B[3,5-(CF_3)_2C_6H_3]_4]$, $(C_6H_5S)C_6H_4S(C_6H_5)_2[B[3,5-(CF_3)_2C_6H_3]_4]$, $(C_2H_5)_3NH[B[3,5-(CF_3)_2C_6H_3]_4]$, $C_6H_5N_2[B[3,5-(CF_3)_2C_6H_3]_4,]$ $(C_6H_5)_3P(CH_3)[B[3,5-(CF_3)_2C_6H_3]_4]$, $(C_2H_5)_3NH[B(CH_3)(C_6F_5)_3]$, $(C_6H_5)_2I[B(CH_3)(C_6F_5)_3]$, $(C_6H_5)_3S[B(CH_3)(C_6F_5)_3]$, $(C_6H_5)_3S[B(n-butyl)(C_6F_5)_3]$, $C_6H_5N(CH_3)_2H[B[3,5-(CF_3)_2C_6H_3]_4]$, $C_5H_5NH[B[3,5-(CF_3)_2C_6H_3]_4]$, $C_6H_5N(CH_3)_2H[B(C_6F_5)_4]$, and $C_6H_5N(CH_3)_2H[B(CH_3)C_6F_5]_3]$.

(3) Organometallic Salts

Examples of organometallic salts include but are not limited to: $(C_5H_5)$(benzene)$Fe[B[3,5-(CF_3)_2C_6H_3]_4]$, $(C_5H_5)$(mesitylene)$Fe[B[3,5-(CF_3)_2C_6H_3]_4]$, $(C_5H_5)$(toluene)$Fe[B[3,5-(CF_3)_2C_6H_3]_4]$, $(C_5H_5)$(p-xylene)$Fe[B[3,5-(CF_3)_2C_6H_3]_4]$, $(C_5(CH_3)_5)$(benzene)$Fe[B[3,5-(CF_3)_2C_6H_3]_4]$, (benzene)$Mn(CO)_3[B[3,5-(CF_3)_2C_6H_3]_4]$, (toluene)$Mn(CO)_3[B[3,5-(CF_3)_2C_6H_3]_4]$, (benzene)$_2Fe[(B[3,5-(CF_3)_2C_6H_3]_4)_2]$, $(C_5H_5)Fe(CO)_3[B[3,5-(CF_3)_2C_6H_3]_4]$, $(C_5H_4CH_3)Fe(CO)_3[B[3,5-(CF_3)_2C_6H_3]_4]$, $(C_5H_4CH_3)Mn(CO)_2(NO)[B[3,5-(CF_3)_2C_6H_3]_4]$, $(C_5H_4CH_3)_2Fe[B[3,5-(CF_3)_2C_6H_3]_4]$, (toluene)$_2Cr[B[3,5-(CF_3)_2C_6H_3]_4]$, $(C_5H_5)$(p-xylene)$Fe[B(C_6F_5)_4]$, (benzene)$Mn(CO)_3[B(C_6F_5)_4]$, (mesitylene)$Mn(CO)_3[B(C_6F_5)_4]$, (toluene)$_2Fe[(B(C_6F_5)_4)_2]$, $(C_5H_5)Fe(CO)_3[B(C_6F_5)_4]$, $(C_5H_5)_2Fe[B(C_6F_5)_4]$, $(C_5H_5)Fe(CO)_2(P(C_6H_5)_3)[B(C_6F_5)_4]$, $(C_5H_5)$(toluene)$Fe[B(CH_3)(C_6F_5)_3]$, (benzene)$Mn(CO)_3[B(CH_3)(C_6F_5)_3]$, (benzene)$Mn(CO)_3[BF(C_6F_5)_3]$, and $(C_5H_5)$(mesitylene)$Fe[BF(C_6F_5)_3]$.

Methods of Use and Preparation

Catalysts

In general, catalyst or initiator salts of the instant invention can be prepared by anion exchange or metathesis reactions by combining initiator or catalyst salts that contain conventional counteranions, such as chloride, $PF_6^-$, $SbF_6^-$ or $BF_4^-$, with simple salts, such as alkali or alkaline earth metal salts or alkylammonium salts, of the nonnucleophilic anions of the invention in a suitable solvent. Generally, metathesis reactions may be carried out at temperatures ranging from about −80° to about 100° C., preferably at ambient temperature, under conditions in which either the initiator/catalyst salt of the instant invention or the metathesis byproduct(s) selectively precipitates, thus permitting isolation of the salt of the invention in the form of a solution or a pure solid. Alternatively, anion metathesis may be achieved by passing a solution of a background art initiator or catalyst salt through a column of an insoluble anion exchange resin containing a nonnucleophilic anion of the invention. It will, of course, be appreciated that the catalyst/ initiator salts of the invention will form in situ if the individual components described supra are added directly to the polymerization process and a suitable solvent or diluent, including monomer, is used in the polymerization process. It is preferred, however, to form the pure catalyst or initiator in a separate step as a solid or in a suitable solvent prior to adding the same to the polymerizable composition and performing the polymerization process.

Suitable metathesis solvents generally are capable of dissolving at least one and preferably all of the reagents required for the metathesis reaction without reacting with these reagents. Solvents are generally selected such that the desired salt or the metathesis byproducts selectively precipitate, thus allowing the desired salt to be isolated in relatively pure form. Normally, the preferred solvent for a particular system is determined empirically. In the cases where an anion exchange resin is used, the solvent should not dissolve the resin, but should dissolve the metathesis reagents and the desired product salt. Nonlimiting examples of suitable solvents include, water; chlorocarbons, such as methylene chloride, and chloroform; ethers; aromatic hydrocarbons, such as toluene, and chlorobenzene; nitriles, such as, acetonitrile; alcohols, such as methanol and ethanol; nitrobenzene; nitromethane; ketones, such as acetone and methyl ethyl ketone; and other similar classes of organic solvents. Mixtures of solvents are often desirable to control solubility of reagents and product salts.

Polymerizable Compositions and Polymers

The present invention also provides polymerizable compositions comprising (a) at least one of cationic addition polymerizable monomers, ethylenically-unsaturated free radical monomers, mixtures of multifunctional monomers polymerizable by catalyzed step-growth polymerization or mixtures thereof and (b) a catalyst or initiator salt of the present invention and a method for the polymerization comprising the steps of:

(a) providing a monomer mixture comprising at least one of a cationically polymerizable monomer, an ethylenically-unsaturated free radical monomer, or mixtures of multifunctional monomers polymerizable by catalyzed step-growth polymerization and mixtures thereof, (b) adding a catalytically effective amount of a curing agent to the monomer mixture wherein the curing agent comprises at least one of the initiator or catalyst salts of the instant invention (and all permutations of the order of mixing the aforementioned components), thereby forming a polymerizable composition, and (c) allowing the polymerizable composition to polymerize or adding a sufficient amount of energy to the mixture to effect polymerization.

The present invention further provides a method for preparing coated articles containing the cured composition of the invention comprising the steps of:

(a) providing a substrate, (b) coating an energy polymerizable composition of step (b) as described above onto at least one surface of the substrate by methods known in the art, such as bar, knife, reverse roll, knurled roll, curtain, or spin coatings, or by dipping, spraying, brushing, and the like, with or without a coating solvent, and (c) applying energy (after evaporation of solvent, if present) to the coating and, if desired, to the article to cause the polymerization of the coating.

It may be desirable to add solvent to solubilize components and aid in processing. Solvent, preferably organic solvent, may be present in an amount up to 99 weight percent, preferably in the range of 0 to 90 weight percent, and most preferably in the range of 0 to 75 weight percent, of the polymerizable composition can be used.

In the polymerizable compositions of this invention, the catalyst or initiator salts can be present in a catalytically effective amount to initiate polymerization, and is generally in the range of 0.01 to 20 weight percent (wt %), preferably 0.1 to 10 wt % of the total composition.

Cationically Polymerizable Monomers

A wide variety of monomers can be energy polymerized using the catalysts and initiators of the invention. Suitable cationically polymerizable monomers and/or oligomers typically contain at least one cationically polymerizable group such as epoxides, cyclic ethers, vinyl ethers, vinylamines, unsaturated hydrocarbons, lactones and other cyclic esters, lactams, cyclic carbonates, cyclic acetals, aldehydes, cyclic amines, cyclic sulfides, cyclosiloxanes, cyclotriphosphazenes and other cationically polymerizable groups or monomers described in G. Odian, "Principles of Polymerization" Third Edition, John Wiley & Sons Inc., 1991, N.Y. and "Encyclopedia of Polymer Science and Engineering", Second Edition, H. F. Mark, N. M. Bikales, C. G. Overberger, G. Menges, J. I. Kroschwitz, Eds., Vol. 2, John Wiley & Sons, 1985, N.Y., pp. 729–814.

Particularly useful examples include cyclic ether monomers, including epoxide monomers and are described in U.S. Pat. No. 4,985,340 and such description is incorporated herein by reference, vinyl organic monomers are described in U.S. Pat. No. 4,264,703, and such description is incorporated herein by reference.

Free-radically Polymerizable Monomers

Suitable free-radically polymerizable compounds containing at least one ethylenically unsaturated double bond, may be monomers and/or oligomers, such as acrylates and methacrylates, acrylamides, methacrylamides, and other vinyl compounds capable of undergoing free-radical polymerization. Such monomers and specific examples are more fully described in U.S. Pat. No. 4,985,340, and such description is incorporated herein by reference.

Catalyzed Step Growth Polymerizable Monomers

Catalyzed step growth polymerizations include but are not limited to, the reaction of multifunctional isocyanates (polyisocyanates) with multifunctional alcohols (polyols) to form polyurethanes, the reaction of multifunctional epoxies with multifunctional alcohols, and the cyclotrimerization of multifunctional cyanate esters to crosslinked polytriazine resins.

Particularly useful multifunctional alcohol, isocyanate, and epoxide components that can be cured by catalyzed step-growth polymerization using catalysts of the present invention are described in U.S. Pat. Nos. 4,985,340, 4,503,211 and 4,340,716, and such description is incorporated herein by reference.

Suitable multifunctional cyanate esters that can be cured by catalyzed cyclotrimerization, using catalysts of this invention are described in U.S. Pat. Nos. 5,143,785 and 5,215,860 and such description is incorporated herein by reference.

Where mixtures of two or more polymerizable monomers are used in combination, the polymerizable components can be present in any proportion preferably with the minor component comprising at least 1.0 wt %.

Mixtures of aforementioned classes of monomers with additives such as tackifiers, hardeners, co-curatives, curing agents, stabilizers, sensitizers etc. can also be used in the polymerizable compositions of this invention. Furthermore, adjuvants, such as pigments, abrasive granules, stabilizers, light stabilizers, antioxidants, flow agents, bodying agents, flatting agents, colorants, inert fillers, binders, blowing agents, fungicides, bacteriocides, surfactants, plasticizers, and other additives as known to those skilled in the art can be added to the compositions of this invention. These can be added in an amount effective for their intended purpose.

Optionally, it is within the scope of this invention to include photosensitizers or photoaccelerators in the radiation-sensitive compositions. Use of photosensitizers or photoaccelerators alters the wavelength sensitivity of radiation-sensitive compositions employing the latent catalysts and initiators of this invention. This is particularly advantageous when the latent catalyst or initiator does not strongly absorb the incident radiation. Use of photosensitizers or photoaccelerators increases the radiation sensitivity, allowing shorter exposure times and/or use of less powerful sources of radiation. Any photosensitizer or photoaccelerator may be useful if its triplet energy is at least 45 kilocalories per mole. Examples of such photosensitizers are given in Table 2-1 of the reference Steven L. Murov, Handbook of photochemistry, Marcel Dekker Inc., N.Y., 27–35 (1973), and include those described in U.S. Pat. No. 4,985,340, and such description is incorporated herein by reference. When present, the amount of photosensitizer or photoaccelerator used in the practice of the present invention is generally in the range of 0.01 to 10 and preferably 0.1 to 1.0 wt % of photosensitizer or photoaccelerator based on the weight of the curable composition.

Solvents, preferably organic, can be used to assist in dissolving the curing agent in the polymerizable monomers described supra and as a processing aid. Representative solvents include acetone, methyl ethyl ketone, cyclopentanone, methyl cellosolve acetate, methylene chloride, nitromethane, methyl formate, acetonitrile, gamma-butyrolactone, and 1,2-dimethoxyethane (glyme). In some applications it may be advantageous to adsorb the curing agents onto an inert support such as silica, alumina, clays, etc., as described in U.S. Pat. No. 4,677,137.

In general, energy-induced polymerization of the polymerizable compositions of this invention, which incorporate a latent, light or radiation sensitive catalyst or initiator, may be carried out at room temperature for the majority of energy curable compositions, although low temperature (e.g., −10° C.) or elevated temperature (e.g., 30° to 400° C., preferably 50° to 300° C.) can be used to subdue the exotherm of polymerization or to accelerate the polymerization, respectively. Temperature of polymerization and amount of catalyst will vary and be dependent on the particular curable composition used and the desired application of the polymerized or cured product. The amount of curing agent (catalyst or initiator) to be used in this invention should be sufficient to effect polymerization of the monomers (i.e., a catalytically effective amount) under the desired use conditions. Such amount generally will be in the range of about 0.01 to 20 wt %, and preferably 0.1 to 10 wt %, based on the weight of the curable composition.

For those compositions of the invention that are radiation sensitive, any source of radiation including accelerated particles (e.g., electron beam radiation) and radiation sources emitting active radiation in the ultraviolet and visible region of the spectrum (e.g., about 200 nm to 800 nm) can be used. Suitable sources of radiation include fluorescent lamps, mercury vapor discharge lamps, carbon arcs, tungsten lamps, xenon lamps, lasers, sunlight, etc. The required amount of exposure to effect polymerization is dependent upon such factors as the identity and concentrations of the curing agent, the particular monomers, the temperature and thickness of the exposed material, type of substrate, intensity of the radiation source and the amount of heat associated with the radiation. Thermal polymerization using direct heating or induction heating, infrared or microwave electromagnetic radiation, as is known in the art, can be used to cure the compositions according to the teachings of this invention. Curing conditions, for both photocuring and thermal curing, including duration, wavelength, temperature are readily ascertainable by those skilled in the art.

It is within the scope of this invention to include two-stage polymerization (curing), by first activating the curing agent by irradiating the curable compositions and subsequently thermally curing the activated precursors so obtained, the irradiation temperature being below the temperature employed for the subsequent heat-curing. The activated precursors may normally be cured at temperatures that are substantially lower than those required for the direct thermal curing, with an advantage in some cases in the range from 50° to 110° C. This two-stage curing also makes it possible to control the polymerization in a particularly simple and advantageous manner.

Certain of the catalysts and initiator salts of this invention, particularly those possessing anions that contain a multiplicity of perfluorinated or $CF_3$-substituted aromatic hydrocarbon rings bound to a central metal or metalloid core, display dramatically improved solubility in monomers commonly used in cationic, or free-radical addition polymerization or catalyzed step-growth polymerization, as well as in common organic solvents and diluents, when compared to initiator salts known in the art that contain the same cationic portion but more conventional counteranions, such as $SbF_6^-$ or $PF_6^-$. The catalyst and initiator salts of this invention are generally at least 5 times, advantageously at least 10 times, and in many cases at least 50 times more soluble than analogous $SbF_6^-$ salts in organic monomers and solvents. For example, initiators of this invention, such as $(C_6H_5)_2I$ $[B[3,5-(CF_3)_2C_6H_3]_4]$ and $(C_6H_5)_2I[B(C_6F_5)_4]$, display solubilities in methylene chloride and diethyl ether approximately 100 times or more greater on a weight percent basis than the solubility of $(C_6H_5)_2I[SbF_6]$ under identical conditions. This enhanced solubility of catalysts and initiators in common monomers represents an important advance over the art, particularly for applications where it is desirable to minimize or eliminate the use of toxic or environmentally harmful volatile organic solvents or diluents, often added to monomer mixtures to promote initiator solubility. Alternatively, in applications involving highly non-polar monomers, such as epoxy-functional silicones, multifunctional unsaturated hydrocarbons, unsaturated or epoxidized triglycerides (supra), the initiators provide an alternative to the synthetic introduction of solubilizing substituents onto the cationic portion of the initiator. While this is commonly practiced, it often requires elaborate and expensive synthetic techniques. For example, $(C_6H_5)_2I[B[3,5-(CF_3)_2C_6H_3]_4]$ and $(Aryl)_3S$ $[B[3,5-(CF_3)_2C_6H_3]_4]$ salts of this invention display solubility and photocuring activity in commercially available epoxy-functional silicones such as UV 9300 (General Electric Co.), epoxy-functional isoprene copolymers such as Epoxidized Kraton™ Polymer EKP-102 (Shell Chemical) and unsaturated hydrocarbons such as β-pinene, despite the absence of solubilizing substituents on the cationic portion of the photoinitiator salts.

A particularly surprising feature of certain onium and cationic organometallic photoinitiator salts of the anions $[3,5-(CF^3)_2C_6H_3]_4B^-$ and $(C_6F_5)_4B^-$, is their greater photopolymerization or photocuring activity, and wavelength response compared to corresponding salts of more conventional anions. The enhanced photoactivity of photoinitiators of this invention is especially notable when the photoinitiators are used in photopolymerizable compositions containing monomers that polymerize via cationic addition polymerization.

The use of certain onium and organometallic photoinitiator salts of the instant invention in polymerizable compositions containing cationically polymerizable monomers, optionally further containing solvents, diluents, other types of monomers or additives, such as photosensitizers, provide numerous advantages including: (1) shorter photocure times (irradiation time required for onset of cure or polymerization) under constant irradiation, (2) more complete curing (i.e., greater extent of polymerization or larger polymerization exotherm) at equivalent radiation dosages, and (3) superior light absorption (higher extinction coefficients) in the 200 to 400 nm wavelength range, when compared to art known photoinitiators, containing the same cationic portion but more conventional counteranions, such as $SbF_6^-$, at equimolar concentrations of initiator and under identical reaction conditions. Given that onium and organometallic salts of $SbF_6^-$ are reported to be the most reactive cationic photoinitiators of the art and the unobserved effect of counteranions on the photochemistry of cationic initiators, the superior photoreactivity displayed by certain photoinitiators of the instant invention, differing only in the composition of the counteranion, represents an unexpected, and significant advance in processes requiring short exposure times, greater cure speed or photoefficiency, or equivalent cure speeds with lower initiator or catalyst residues, or in processes where the addition of additives such as photosensitizers, to improve photoactivity, would be undesirable.

Another advantage offered by certain catalyst and initiator salts of the instant invention, particularly those in which the anion is one of the preferred boron centered anions as compared to certain well-known anions, particularly $SbF_6^-$ and $AsF_6^-$, is the exclusion in the former case of highly toxic elements such as antimony and arsenic, which pose environmental and health risks and limit the commercial utility of the most reactive initiators of the art.

Catalysts or initiators of this invention that incorporate the preferred boron-centered anions, particularly $[3,5-(CF_3)_2C_6H_3]_4B^-$ and $(C_6F_5)_4B^-$, are relatively inert toward hydrolysis, which, by contrast, is known to readily occur in certain initiator compositions known in the art that utilize $SbF_6^-$, $AsF_6^-$ and $PF_6^-$ anions to form highly toxic and corrosive hydrofluoric acid. Furthermore, even if anion hydrolysis in the case of the present invention initiators were to eventually occur, no readily accessible chemical pathway to hydrofluoric acid is available. Hence, in applications where the toxic or corrosive effects of hydrofluoric acid are a concern, such as those in which the initiators may be in contact with metallic or glass substrates, electronic components, an acid-sensitive polymer or living tissue, the use of initiator or catalyst compositions of this invention would provide a distinct advantage, while at the same time providing equivalent or better reactivity.

Triarylsulfonium salts of this invention that employ the preferred boron-centered anions, particularly $[3,5-(CF_3)_2C_6H_3]_4B^-$, have improved thermal stability, as compared to the corresponding $SbF_6^-$ salts. Advantageously, this improved thermal stability permits their use in applications requiring high temperature processing without premature curing of the polymerizable composition or degradation of the photochemical reactivity of the catalyst or initiator.

As in the case of photoactivated curing agents of this invention, certain thermally-activated catalyst and initiator salts of the invention also display improved curing activity, as determined, for example, by differential scanning calorimetry (DSC) measurement of the magnitude of curing exotherms, when compared to polymerizable compositions containing analogous salts known in the art comprising the same cationic portion, but a more conventional counteranion.

Certain onium-containing initiator and catalyst salts of this invention containing at least one $N^+$-H subunit as part of the cationic portion, in particular, alkyl and aryl ammonium salts or protonated heterocyclic amine salts of $[3,5-(CF_3)_2C_6H_3]_4B^-$, have shown improved activity for thermally activated, cationic addition polymerization of monomers such as epoxides or thermally activated, catalyzed, step-growth polymerization of epoxy/alcohol monomer mixtures. Like the other initiators and catalysts of this invention, the mono-, di-, or tri-protic, nitrogen onium salts of this invention provide improved solubility in organic solvents and monomers. An additional feature of this particular class of salts is the level of control of cure temperature provided. Simple structural modifications to the nitrogen-based cation can produce a significant change in the temperature at which the initiator will induce curing of a monomer. Furthermore, the changes in cure temperature correlate well with the change in thermodynamic acidity ($pK_a$) of the protic nitrogen cation, based upon literature values of $pK_a$'s in aqueous media. Thus, the structures of the cationic portions of these salts may be tailored to achieve thermally induced or catalyzed curing at specific temperatures, depending upon the desired application, ranging from about normal ambient temperatures to about 200° C. These salts may further be used in conjunction with additives such as neutral amines, as described in the art (UK 963,058) to provide additional control of cure temperature and shelf life.

Alternatively, the catalyst and initiator salts comprising a nonnucleophilic anion of this invention and a cationic portion that is a monovalent or polyvalent metal cation selected from the group consisting of metals of Groups IA–IIIA, IB–VIIB, VIII and those of the lanthanide and actinide series of the Periodic Table of the Elements can, upon application of heat, induce the polymerization of cationically sensitive monomers, such as epoxides and vinyl ethers. Surprisingly, with certain alkali metal salts, such as $Na^+$ or $Li$ $[B[3,5-(CF_3)_2C_6H_3]_4]$, the rates of epoxy polymerization are slow and gradual and proceed without significant reaction exotherm, even in pure cyclohexene oxide monomer and at highly elevated temperatures ranging from 100° to 200° C. This contrasts sharply with conventional epoxy polymerization initiators known in the art, as well as other epoxy polymerization initiators of the present invention, which generally induce extremely rapid and highly exothermic epoxide polymerization, particularly in the case of cycloaliphatic epoxies and polymerizations initiated at elevated temperatures. The rate of polymerization increases with increasing temperature, therefore, the rate and extent of epoxy polymerization can be easily controlled using the metal salts of this invention by merely controlling the process temperature and the duration of heating. Polymerization rates also vary as a function of the metal cation employed. The unique reactivity of this particular class of initiators or catalysts is particularly useful for applications where an extended shelf life or gradual curing is desired, large reaction exotherms can not be tolerated, or where only partial polymerization or curing of an epoxy is desired to, for example, modify viscosity prior to coating.

Compositions of this invention are useful for coatings, foams, shaped articles, adhesives, filled or reinforced composites, abrasives, caulking and sealing compounds, casting and molding compounds, potting and encapsulating compounds, impregnating and coating compounds, and other applications which are known to those skilled in the art.

Compositions of this invention may be applied, preferably as a liquid, to a substrate such as steel, aluminum, copper, cadmium, zinc, ceramic, glass, paper, wood or various plastic films such as poly(ethylene terephthalate), plasticized poly(vinylchloride), polypropylene, polyethylene, and the like, and irradiated. By polymerizing part of the coating, as by irradiation through a mask, those sections which have not been exposed may be washed with a solvent to remove the unpolymerized portions while leaving the photopolymerized, insoluble portions in place. Thus, compositions of this invention may be used in the production of articles useful in the graphic arts and electronics industry such as printing plates and printed circuits. Methods of producing printing plates and printed circuits from photopolymerizing compositions are well known in the art (cf., British Patent Specification No. 1,495,746).

Objects and advantages of this invention are further illustrated by the following examples, but the particular materials and the amounts thereof recited in these examples, as well as other conditions and details, should not be construed to unduly limit this invention.

Examples

The following examples provide a synthetic procedure for the compositions of the present invention. That procedure, with the selection of the appropriate reagents and conditions is believed to be representative of the synthesis of the members of the generic class of compounds of the present invention.

All examples were prepared and evaluated in ambient atmosphere (without deliberate exclusion of oxygen and water vapor) unless indicated otherwise or apparent. Organic solvents used in polymerization experiments were obtained in anhydrous form and used without further purification. Liquid monomers polymerizable by cationic addition polymerization were generally dried by storage over activated, 3 or 4 Angstrom molecular sieves. Organometallic chloride ($Cl^-$), hexafluorophosphate ($PF_6^-$) and hexafluoroantimonate salts ($SbF_6^-$) used as precursors to the curing agents of this invention or in the comparative examples were prepared following techniques well known in the art, unless otherwise stated (c.f., Dietliker, "Chemistry and Technology of UV and EB Formulation for Coatings, Inks and Paints," Vol. 3, "Photoinitiators for Free Radical and Cationic Polymerization," SITA Technology Ltd., 1991, London, pp 433–434 and references cited therein; U.S. Pat. No. 5,059, 701; Brookhart et al., Organometallics, 2, 638 (1983); Pauson et al., J. Chem. Soc., Dalton Trans., 1677 and 1683 (1975)).

Sodium and lithium salts of $[3,5-(CF_3)_2C_6H_3]_4B^-$ ($TFPB^-$) used in the examples were prepared following published techniques (H. Kobayashi et al., Bull. Chem. Soc. Japan, 57, 2600 (1984)). Diphenyliodonium chloride, purchased from Aldrich, was used as a precursor in the preparation of corresponding $PF_6^-$, $SbF_6^-$, $[3,5-(CF_3)_2C_6H_3]_4B^-$, and $(C_6F_5)_4B^-$ salts. Triarylsulfonium chloride, stated by the manufacturer to be a mixture of triphenylsulfonium chloride (1–5 %), diphenyl[(4-phenylthio)phenyl]sulfonium chloride (15–20%), and (thiodi-4,1-phenylene)bis(diphenylsulfonium) dichloride (25–30%) in aqueous solution, was obtained from Fine Organics Ltd. (Middlesbrough, Cleveland TS2 1UB, England), all percentages being expressed as weight percents in water. The latter commercial mixture was used as a precursor for preparing corresponding $SbF_6^-$, $[3,5-(CF_3)_2C_6H_3]_4B^-$, $(C_6F_5)_4B^-$ and $(n-butyl)(C_6F_5)_3B^-$ salts.

Protic, nitrogen-based onium salts were generally prepared by protonation of the nitrogen center of the neutral precursors with strong acid followed by solvent evaporation or precipitation with the desired anion. The introduction of nonnucleophilic anions to provide initiator salts used in the present invention was accomplished using standard anion metathesis reactions as illustrated in the following Examples.

All photoinitiators and their solutions in monomers were handled under subdued lights, that is, a light intensity below the level necessary to initiate polymerization. Solutions were stored in the dark or in amber glass bottles. Initiator and catalyst salts of the invention were characterized by $^1H$, $^{11}B$, and $^{13}C$ NMR spectroscopy. The $(C_6F_5)_4B^-$ and $(n-butyl)(C_6F_5)_3B^-$ salts of Examples 7 and 8 were further characterized by elemental analysis.

Designation of an example designated with a number, for example, "15" indicates an example illustrative of the present invention. When an example is prefixed with the letter "C", for example "C15", the example is a comparative example.

| Glossary | |
|---|---|
| TFPB | [3,5-(CF$_3$)$_2$C$_6$H$_3$]$_4$B$^-$ |
| PFTPB | (C$_6$F$_5$)$_4$B$^-$ |
| DGEBA | diglycidylether of bisphenol A (commercially available from Shell Chemical Co. under the trade designation of EPON™ 828 (eq. wt. = 185–192 g/eq.)) |
| ERL4221 | 3,4-epoxycyclohexylmethyl-3,4-epoxycyclohexane carboxylate (commercially available from Union Carbide under the trade designation of ERL™ 4221 (eq. wt. = 133 g/eq.)) |
| ERL4299 | bis-(3,4-epoxy-cyclohexylmethyl)adipate (commercially available from Union Carbide under the trade designation of ERL™ 4299 (eq. wt. = 183 g/eq.)) |
| SR295 | pentaerthyritol tetraacrylate (commercially available from Sartomer Chemical under the trade designation of SR295) |
| L-10 | 1,1-bis(4-cyanatophenyl)ethane, a liquid cyanate ester resin (commercially available from Ciba-Geigy) |
| KB-1 | 1,1-dimethoxy-1-phenylacetophenone (commercially available from Sartomer Chemical) |
| C$_5$Me$_5$ | pentamethylcyclopentadienyl |
| C$_5$H$_4$CH$_3$ | methylcyclopentadienyl |
| C$_6$H$_5$ | phenyl |
| CH$_3$—C$_6$H$_4$ | p-tolyl |
| C$_2$H$_5$ | ethyl |
| C$_6$F$_5$ | pentafluorophenyl |
| 3,5-(CF$_3$)$_2$C$_6$H$_3$ | 3,5-bis(trifluoromethyl)phenyl |
| Cp | cyclopentadienyl (C$_5$H$_5$) |
| Me | methyl |
| Ph | phenyl |

Example 1

Preparation of (mesitylene)(cyclopentadienyl)iron [B[3,5-(CF$_3$)$_2$C$_6$H$_3$]$_4$]

The iron salt was prepared by combining 0.095 gram of (mesitylene)(cyclopentadienyl)iron chloride with 0.323 gram of Na [3,5-(CF$_3$)$_2$C$_6$H$_3$]$_4$B(3H$_2$O) in 20 mL of methylene chloride. This mixture was stirred at room temperature in the dark for approximately 5 hours. Sodium chloride precipitated during the reaction and was removed by filtration of the solution by suction through Celite. The filtrate was then evaporated to dryness at a temperature of 35° C. and a pressure of 2.6 kPa to give a yellow, solid product. Residual moisture was removed by evacuation to 1.33 Pa on a vacuum line equipped with a liquid nitrogen trap for 15 minutes at room temperature. This produced a final yield of 0.313 gram of pure, yellow, solid product. The [(mesitylene)(cyclopentadienyl)iron] [B[3,5-(CF$_3$)$_2$C$_6$H$_3$]$_4$] salt displayed very high solubility in organic solvents such as ethyl acetate compared to corresponding chloride and SbF$_6^-$ salts. Using NMR spectroscopy, it was determined that the solid product was stable for at least 2 years under ambient conditions in the dark.

Example 2

Preparation of [diphenyliodonium] [B[3,5-(CF$_3$)$_2$C$_6$H$_3$]$_4$]

The iodonium salt was prepared by combining 2.40 grams of diphenyliodonium chloride with 7.00 grams of Na [3,5-(CF$_3$)$_2$C$_6$H$_3$]$_4$B] (3H$_2$O) in 220 mL of methylene chloride. The mixture was stirred at room temperature in the dark for approximately 26 hours. Sodium chloride precipitated during the reaction and was removed by gravity filtration through fluted filter paper. To the filtrate was added 200 mL of hexane. The resulting solution was then concentrated to approximately 20 mL on a rotary evaporator at a temperature of 35° C. and a pressure of 2.7 kPa producing a white solid precipitate. The solid was suspended in an additional 100 mL of hexane and filtered by suction. The collected white solid was washed with three 50 mL portions of fresh hexane and then dried partially by suction. The product was further dried at 1.33 Pa and 60°–80° C. for 3 hours in a vacuum oven equipped with a liquid nitrogen trap. The dry [diphenyliodonium] [B[3,5-(CF$_3$)$_2$C$_6$H$_3$]$_4$] salt was recovered as a white powder with a final yield of 8.253 grams.

Example 3

Preparation of [(benzene)Mn(CO)$_3$] [B[3,5-(CF$_3$)$_2$C$_6$H$_3$]$_4$]

The manganese salt was prepared by combining in an amber bottle 1.174 grams of [(benzene)Mn(CO)$_3$]PF$_6$ with 3.000 grams Na [3,5-(CF$_3$)$_2$C$_6$H$_3$]$_4$B](3H$_2$O) in 125 mL of methylene chloride. The mixture was agitated at room temperature for approximately 50 minutes. Sodium hexafluorophosphate precipitated during the metathetical reaction and was removed by gravity filtration through fluted filter paper. The filtrate was treated with 325 mL of hexane, producing a finely divided, light yellow precipitate. The precipitate was collected by suction filtration through a sintered glass frit, washed with additional hexane, and partially dried by suction. The product was further dried at 1.33 Pa and 80°–84° C. for 18 hours in a vacuum oven equipped with a liquid nitrogen trap. The dry [(benzene)Mn(CO)$_3$] [B[3,5-(CF$_3$)$_2$C$_6$H$_3$]$_4$] salt was recovered as a pale yellow, microcrystalline solid, with a final yield of 3.316 grams.

Example 4

Preparation of (aryl)$_3$S [B[3,5-(CF$_3$)$_2$C$_6$H$_3$]$_4$]

The sulfonium salt was comprised of a mixture of cationic sulfonium species including triphenylsulfonium (about 9 mole %), diphenyl[(4-phenylthio)phenyl]sulfonium (about 38 mole %), and (thiodi- 4,1-phenylene)bis(diphenylsulfonium) (about 53 mole %) cations derived from a mixture commercially available from Fine Organics Ltd. containing similar proportions of the respective chloride salt precursors as a 50% by weight solution in water.

Synthesis was achieved by diluting 5.7 mL of the commercial, aqueous sulfonium chloride salt mixture in 100 mL of distilled water. This solution was combined, at room temperature in the dark, with a solution of 10.00 grams Na [3,5-(CF$_3$)$_2$C$_6$H$_3$]$_4$B] (3H$_2$O) in 6.0 mL of methanol by slow addition of the latter while rapidly stirring. (Aryl)$_3$S [B[3,5-(CF$_3$)$_2$C$_6$H$_3$]$_4$] salt precipitated immediately as a white solid and was allowed to settle for approximately 10 minutes. The supernatant liquid was then decanted. The remaining solid was washed with a 100 mL portion of distilled water, and then the water was decanted. The solid was combined with another 100 mL portion of distilled water, the mixture was stirred briefly, and the solid recovered by suction filtration through a glass frit. The solid was partially dried by suction and then more thoroughly dried at 1.33 Pa and 97°–110° C. for a total of 36 hours in a vacuum oven equipped with a liquid nitrogen trap. (Aryl)$_3$S [B[3,5-(CF$_3$)$_2$C$_6$H$_3$]$_4$] salt was recovered as a white powder in a yield of approximately 8.0 grams. IR spectroscopic analysis of a concentrated Nujol mull indicated that the product was anhydrous.

Example 5

Preparation of [Li[B($C_6F_5$)$_4$]]2($C_2H_5$)$_2$O $C_6F_5$Li (70 mmole) was prepared according to the method described by A. G. Massey and A. H. Park, Organometallic Syntheses, 3, 461 (1986), modified by using a mixture of 200 mL of hexane and 50 mL of diethyl ether as the solvent. To the mixture at a temperature of −78° C. was added dropwise 17.5 mL of 1.0M $BCl_3$ in hexane. After stirring overnight, crude product was collected on a Schlenk filter and vacuum dried. The crude material was purified by Soxhlet extraction under vacuum with anhydrous methylene chloride to produce a white, powdery product. This was dried under high vacuum producing a yield of 13 grams (77%). $^1$H NMR analysis showed the product to contain 2.1 moles of diethyl ether per formula weight. Because the product was hygroscopic, it was stored under dry nitrogen.

Example 6

Preparation of Li [B(n-butyl)($C_6F_5$)$_3$]

To a stirred suspension of 1.17 grams (2.3 mmoles) ($C_6F_5$)$_3$B in 10 mL of hexane was added 0.95 mL of a 2.5M solution of n-butyllithium in hexane under nitrogen. The white solid product precipitated and after 30 minutes it was isolated by filtration and washed with 5 mL hexane. After vacuum drying, the yield was 0.98 gram. $^{11}$B NMR (toluene): −7.7 (s) ppm.

Example 7

Preparation of [(Aryl)$_3$S] [B(n-butyl)($C_6F_5$)$_3$]

A mixture of 0.90 gram (1.6 mmoles) Li[B(n-butyl)($C_6F_5$)$_3$], 0.78 gram (1.56 mmoles) (aryl)$_3$S [$SbF_6$] and 10 mL anhydrous methylene chloride was stirred for 16 hours in a nitrogen-filled drybox. Filtration afforded 0.34 gram white, insoluble Li [$SbF_6$]. Evaporation of the filtrate left a crude product which transformed into a tacky foam on pumping under high vacuum. $^{11}$B NMR ($CDCl_3$): −13.4 (s) ppm. Elemental Analysis: Calcd (Found) for $C_{40}H_{24}BF_{15}S$; C, 57.7 (54.9); H, 2.9 (3.1).

Example 8

Preparation of [diphenyliodonium] [B($C_6F_5$)$_4$]

The iodonium salt was prepared by combining, under nitrogen, 1.86 grams [Li[B($C_6F_5$)$_4$]] (2$Et_2$O) and 0.63 gram diphenyliodonium chloride in 30 mL anhydrous methylene chloride. After stirring overnight at room temperature, the mixture was filtered. The filtrate was evaporated under vacuum and provided 1.33 grams of white, powdery product. Elemental Anal.: Calcd (Found) for $C_{36}H_{10}BF_{20}I$ C, 45.0 (45.4); H, 1.0 (1.1).

Example 9

Preparation of (aryl)$_3$S [B($C_6F_5$)$_4$]

The sulfonium salt was comprised of a mixture of cationic sulfonium species including triphenylsulfonium (about 9 mole %), diphenyl[(4-phenylthio)phenyl]sulfonium (about 38 mole %), and (thiodi- 4,1-phenylene)bis(diphenylsulfonium) (about 53 mole %) cations derived from a mixture, (commercially available from Fine Organics Ltd.), containing similar proportions of the respective chloride salt precursors as a 50% by weight solution in water.

Synthesis was achieved according to the following procedure: A 1.2 grams sample of [Li($C_6F_5$)$_4$B] (2$Et_2$O) was treated with 2 mL of ethanol followed by 10 mL of water and agitated to dissolve the lithium salt. The resulting solution was added dropwise with stirring to a solution containing 3 mL of the aqueous, 50% triarylsulfonium chloride solution in 20 mL of water. After 40 min, a gelatinous solid was isolated by filtration. The solid was dried at room temperature (with occasional grinding to break up lumps), and then at 130° C. on a diffusion-pumped vacuum line to give 1.1 grams of product as a white solid. Karl-Fischer analysis showed it to be free of water. This salt was hygroscopic and was stored under dry nitrogen.

Example 10

Preparation of (n-butyl)$_3$NH [B[3,5-($CF_3$)$_2C_6H_3$]$_4$]

In an Edenmeyer flask, 0.41 4 gram tri-n-butylamine was dissolved in 15 mL ethanol and 2.3 mL 1.0M aqueous hydrochloric acid was added. In a separate flask 2.00 grams [Na [3,5-($CF_3$)$_2C_6H_3$]$_4$B] (3 $H_2$O) were dissolved in 15 mL ethanol. This solution was subsequently combined with the acidified tri-n-butylamine solution. To the combined solutions was added 60 mL distilled water causing precipitation of an oil. The water/alcohol phase (the upper phase) was decanted and the oil was washed three times with fresh water. After decanting the last water wash, the oil was dissolved in a 80:20 mixture of methylene chloride and toluene. The mixture was then evaporated on a rotary evaporator at 70° C., 2.7 kPa until most of the solvent had been removed and the product crystallized. The residual solvent was removed at 40°–60° C. under high vacuum (1.33 Pa) for 16 hours producing 0.730 gram of a white, crystalline product. Karl-Fischer analysis indicated that the recovered product ((n-butyl)$_3$NH[3,5-($CF_3$)$_2C_6H_3$]$_4$B salt) contained less than 0.08% water by weight.

Example 11

Preparation of [N,N-dimethylanilinium] [B[3,5-($CF_3$)$_2C_6H_3$]$_4$]

In an Erlenmeyer flask, 0.124 gram N,N-dimethylaniline, 0.17 mL 12M aqueous HCl and 10 mL ethanol were combined. In a separate flask, 0.736 gram [Na[3,5-($CF_3$)$_2C_6H_3$]$_4$B](3$H_2$O) was dissolved in 10 mL ethanol. This solution was subsequently combined with the acidified N,N-dimethylaniline solution. To the combined solutions was added 40 mL distilled water dropwise with stirring resulting in separation of an oily precipitate that gradually crystallized. The off-white precipitate was filtered through paper by suction and washed with water. The recovered solid was dried in a vacuum oven for 2 hours at 70° C. and 1.33 Pa giving 0.567 gram of crude product. The product was further purified by dissolution in 10 mL methylene chloride, filtration by suction through a sintered glass frit, and precipitation with 30 mL hexane. The off-white crystalline precipitate was isolated by filtration with a sintered glass frit, washed with hexane, and dried at 70° C., 1.33 Pa for 20 hours in a vacuum oven equipped with a liquid nitrogen trap. Karl-Fischer analysis indicated that the recovered salt ([N,N-dimethylanilinium][3,5-($CF_3$)$_2C_6H_3$]$_4$B salt) contained 1.2% water by weight.

Example 12

Preparation of [2,6-di-t-butyl-4-methylpyridinium] [3,5-($CF_3$)$_2C_6H_3$]$_4$B In an Erlenmeyer flask, 0.305 gram of 2,6-di-t-butyl-4-methylpyridine, 0.20 mL 12M aqueous HCl and 50 mL ethanol were combined. The resulting solution was concentrated on a rotary evaporator to a final volume of 10 mL. In a separate flask, 1.074 gram of Na [[3,5-(CF$_3$)$_2$C$_6$H$_3$]$_4$B](3 H$_2$O) were dissolved in 10 mL ethanol and this solution was subsequently combined with the acidified 2,6-di-t-butyl-4-methyl-pyridine solution. To the combined solutions was added 10 mL distilled water dropwise with stirring resulting in separation of an off-white precipitate. The precipitate was isolated by filtration through a sintered glass frit and washed with fresh water. The recovered solid was dried in a vacuum oven equipped with a liquid nitrogen trap for 16 hours at 70° C. and 1.33 Pa giving 1.218 grams of product. Karl-Fischer analysis indicated that the recovered salt ([2,6-di-t-butyl-4-methylpyridinium] [3,5-(CF$_3$)$_2$C$_6$H$_3$]$_4$B) contained less than 0.05% water by weight.

Example 13

This example illustrates the utility of (Aryl)$_3$S [[3,5-(CF$_3$)$_2$C$_6$H$_3$]$_4$B] for the photoinitiated curing of a highly nonpolar, epoxidized Kraton™ liquid polymer using a minimum amount of co-solvent.

A sample of epoxidized Kraton™ polymer EKP-102, an epoxide functional isoprene copolymer was obtained from Shell Development Company, Houston, Tex. A sample of the liquid polymer (10 grams) was transferred to a vial and combined with 50 mg (aryl)$_3$S [[3,5-(CF$_3$)$_2$C$_6$H$_3$]$_4$B] (prepared as described in Example 4) predissolved in 250 mg methyl ethyl ketone (MEK) to form a homogeneous solution. Portions of this mixture were cast between sheets of silicone-coated polyester release liner to form an approximately 0.5 mm thick liquid film. Both the liquid film and 2.0 grams of the mixture in an open, clear glass vial were irradiated under ambient conditions using a black light fluorescent lamp equipped with two Sylvania, 15 Watt BLB bulbs. After 2 minutes of irradiation, both samples were nearly fully cured producing a solid, nontacky, crosslinked, but flexible polymer.

Examples 14 and C14A–C14B

This example illustrates the improved properties of [(benzene)Mn(CO)$_3$] [[3,5-(CF$_3$)$_2$C$_6$H$_3$]$_4$B] (Example 14) prepared according to Example 3 as a photoinitiator for cyclohexene oxide polymerization compared to analogous art known photoinitiators [(benzene)Mn(CO)$_3$] [PF$_6$] (Comparative Example C14A) and [(mesitylene)Mn(CO)$_3$] [SbF$_6$] (Comparative Example C14B).

Approximately 17 mg of each of the three manganese salts were independently combined with 2.0 mL of neat cyclohexene oxide in 2 dram, clear glass vials and agitated vigorously on a vortex mixer to promote dissolution. Uncapped vials containing the samples were irradiated simultaneously under ambient conditions with a black light fluorescent lamp equipped with two Sylvania, 15 Watt BLB bulbs (# F15T8/BLB). A comparison of the observed relative solubilities, cure times (time required to initiate exothermic curing under constant irradiation), and color of the final polymer are summarized in Table 1.

TABLE 1

| Example | Solubility | Cure Time | Color |
| --- | --- | --- | --- |
| 14 | Complete | 23 seconds | pale yellow |
| C14A | Incomplete | >8 min (no cure) | — |
| C14B | Complete | 110 sec | dark yellow |

Notably, [(benzene)Mn(CO)$_3$] [3,5-(CF$_3$)$_2$C$_6$H$_3$]$_4$B was far more soluble than the PF$_6^-$ salt, which did not appear to dissolve at all, and therefore showed no curing activity. Sufficient solubility was observed with the [(mesitylene)Mn(CO)$_3$] [SbF$_6$] salt. However, it dissolved more slowly and the cure time was nearly a factor of 5 longer than the [3,5-(CF$_3$)$_2$C$_6$H$_3$]$_4$B$^-$ salt. Of the two salts that showed curing activity, the [3,5-(CF$_3$)$_2$C$_6$H$_3$]$_4$B$^-$ salt imparted the lesser amount of color to the final cured composition.

Examples 15–C15

DGEBA-type epoxy resins are widely used epoxy resins because of low cost and their ability to impart excellent physical properties (high strength) to cured compositions. However, DGEBA resins are often slower to polymerize than most cycloaliphatic epoxy resins. This example illustrates the high activity of an organometallic initiator of the present invention, [(benzene)Mn(CO)$_3$] [TFPB] (Example 15) prepared according to Example 3, using thermal curing and two-stage photoactivated curing of a DGEBA resin as compared to analogous art known catalysts, [(mesitylene)Mn(CO)$_3$] [SbF$_6$] (Comparative Example C15). The benzene SbF$_6^-$ salt has limited solubility in the resin, so the mesitylene SbF$_6^-$ salt was evaluated. Relative activities were determined by measuring tack-free cure times.

Curing trials using epoxy solutions of the initiators were conducted in the following manner: Separate epoxy stock solutions were made containing 25 grams DGEBA and 0.125 gram of each initiator. Approximately 0.3 gram of each stock solution was placed in separate aluminum pans to evaluate cure times. When the samples were irradiated, light exposures were made at room temperature with a fluorescent lamp equipped with two 15 Watt, black light bulbs ("BLB") (#F15T8-BL, from General Electric). Samples were subsequently placed on a heated hot plate covered with a large aluminum plate to keep the temperature constant. Three trials per sample were performed and the average time to cure tack-free was recorded. Tack-free cure time was determined by probing the composition with a stick and noting the time when the composition was no longer tacky. Tack-free times are summarized in Table 2 below.

TABLE 2

| Irradiation Conditions | Cure Temperature | Tack-Free Cure Time Example 15 | Tack-Free Cure Time Example C15 |
| --- | --- | --- | --- |
| BLB 5 min. | 100° C. | 4.5 min. | 8.5 min. |
| BLB 5 min. | 150° C. | 21 sec. | 45 sec. |
| Dark | 150° C. | 2.5 min. | >30 min.* |

*The cure time trial was stopped at 30 minutes and the sample was still liquid.

In addition to the significantly faster tack-free cure times provided by the [(benzene)Mn(CO)$_3$] [TFPB] salt, the dilute solution of this salt in the DGEBA resin is virtually colorless, which is an advantage in the manufacture of films and coatings. In contrast, equal weight % solutions of the SbF$_6^-$ salt were light yellow in color.

Examples 16A–16B and C16A–C16B

These examples illustrate the higher thermal activity of organometallic salts of TFPB$^-$ as curing agents for DGEBA epoxy resin as compared to the corresponding art known SbF$_6^-$ salts. Epoxy stock solutions were made containing 20 grams DGEBA epoxy resin, 0.050 gram initiator (organometallic salt) and 0.20 gram butyrolactone solvent (to aid dissolution of the catalyst into the epoxy). Stock solutions were made in subdued light and were stored for a period of hours (less than 2 days) in amber glass bottles at room temperature. Thermal cure temperatures for each initiator and the relative magnitudes of the curing exotherms were determined by differential scanning calorimetry (DSC) without prior photolysis. A DuPont 912 Differential Scanning Calorimeter was used to carry out DSC measurements on initiator-epoxy solutions. Approximately 10 mg of epoxy stock solution were weighed into a standard aluminum boat. The boat was placed in the DSC chamber. An empty boat was used as the reference and was also placed in the DSC chamber. The DSC chamber was closed, and the temperature was ramped at a rate of 10° C. per minute under a continuous nitrogen purge. The DuPont 2100 Thermal Analyst Program was used in data analysis. Measured exotherm parameters included onset temperature, peak temperature, and exotherm energy. Results are summarized in Table 3.

TABLE 3

| Catalyst (Example) | Onset Temperature (°C.) | Peak Temperature (°C.) | Exotherm Energy (J/g) |
| --- | --- | --- | --- |
| Cp(mesitylene)Fe [TFPB] (16A) | 206.3 | 223.7 | 102.1 |
| (benzene)Mn(CO)$_3$ [TFPB] (16B) | 143.4 | 166.6 | 414.4 |
| Cp(mesitylene)Fe [SbF$_6$] (C16A) | 210.6 | 226.8 | 30.0 |
| (mesitylene)Mn(CO)$_3$ [SbF$_6$] (C16B)* | 147.6 | 176.8 | 114.6 |

*Mesitylene was used instead of benzene for solubility reasons.

The onset and peak temperatures for the TFPB$^-$ and SbF$_6^-$ salts are similar. However, the exotherm energies produced by the TFPB$^-$ salts are a factor of 3.4–3.6 greater than those produced by the corresponding SbF$_6^-$ salts, indicating a much greater extent of polymerization or curing using the initiators of the present invention versus the analogous art known initiators.

Examples 17A–17B and C17A–C17B

These examples illustrate the higher thermal activity of photolyzed organometallic salts of TFPB$^-$ as curing agents in two-stage curing (light followed by heat) of DGEBA epoxy resin compared to the corresponding art known SbF$_6^-$ salts.

Epoxy stock solutions were made containing 20 grams DGEBA epoxy resin, 0.050 gram initiator (organometallic salt) and 0.20 gram butyrolactone solvent (to aid dissolution of the catalyst into the epoxy). Stock solutions were made in subdued light and were stored in amber glass bottles at room temperature.

Thermal cure temperatures for each initiator and the relative magnitudes of the curing exotherms were determined by photodifferential scanning calorimetry (PDSC) after sample photolysis. A DuPont 930 Differential Photocalorimeter was used to carry out PDSC measurements on initiator-epoxy solutions. Approximately 10 mg of epoxy stock solution were weighed into a standard aluminum boat, and the boat was placed in the PDSC chamber. An empty boat was used as the reference and was also placed in the PDSC chamber. The chamber was covered with a quartz window and was equilibrated to 25° C. under a nitrogen purge. The chamber was photolyzed for 5 minutes with the 200 Watt mercury arc lamp controlled by the calorimetry unit. After photolysis, the quartz window was removed, the PDSC chamber was closed and the temperature was ramped at a rate of 10° C. per minute under a continuous nitrogen purge. The DuPont 2100 Thermal Analyst program was used in data analysis. Measured exotherm parameters included onset temperature, peak temperature, and exotherm energy. Results are summarized in Table 4.

TABLE 4

| Catalyst (Example) | Onset Temperature (°C.) | Peak Temperature (°C.) | Exotherm Energy (J/g) |
| --- | --- | --- | --- |
| Cp(mesitylene)Fe [TFPB] (17A) | 106.3 | 163.3 | 461.7 |
| (benzene)Mn(CO)$_3$ [TFPB] (17B) | 124.2 | 163.2 | 407.7 |
| Cp(mesitylene)Fe [SbF$_6$] (C17A) | 105.9 | 134.7 | 205.8 |
| (mesitylene)Mn(CO)$_3$ [SbF$_6$] (C17B)* | 115.8 | 143.5 | 158.6 |

*Mesitylene was used instead of benzene for solubility reasons.

The onset and peak temperatures for the photolysed TFPB$^-$ and SbF$_6^-$ salts are similar and, in both cases, occur at significantly lower temperatures than in the unphotolysed cases (Example 16), the latter illustrating the light-activated feature of this system. Notably, the exotherm energies produced by the TFPB$^-$ salts are a factor of 2.2–2.6 greater than those produced by the corresponding SbF$_6^-$ salts, indicating a much greater extent of polymerization or curing in the former case.

Examples 18 and C18

These examples illustrate the advantageous properties of diphenyliodonium TFPB$^-$ (Example 18), compared to art known diphenyliodonium SbF$_6^-$ (Comparative Example C18), in the photoinduced, nonsensitized polymerization of cationically sensitive monomers. Comparative photo-polymerization trials were run on four different monomers (cyclohexene oxide, N-vinyl carbazole, butyl vinyl ether, and β-pinene) representing a broad variety of monomer types known to polymerize by cationic addition polymerization.

Polymerizations were conducted in methylene chloride solution with equimolar concentrations of the diphenyiodonium TFPB$^-$ and SbF$_6^-$ salts using the following procedure: A stock solution of each of the monomers was prepared by combining 12.0 grams of monomer, 4.8 mL of n-heptane (internal GC standard) and 40 mL of anhydrous methylene chloride.

A series of eight clear glass vials (2 drams) was loaded with 0.020 mmoles of photoinitiator (either diphenyliodonium TFPB$^-$ or diphenyliodonium SbF$_6^-$). Each photoinitiator was individually combined with a 7 mL aliquot of each of the monomer stock solutions followed by vigorous agitation to ensure complete dissolution. All eight vials were uncapped, lined up on the base of an inverted fluorescent lamp fixture equipped with two Sylvania F15T8/BLB bulbs and irradiated for a total of 2.0 minutes at room temperature. The elapsed irradiation time required to produce a vigorous polymerization exotherm (usually indicated by sudden and vigorous boiling of the reaction solution) was noted in each case and recorded as the cure time. After 2.0 minutes irradiation period, each of the reaction solutions was quenched by addition of 5 mL of a 10% (wt/vol) buffer solution comprised of equal parts potassium carbonate and potassium bicarbonate in distilled water followed by vigorous agitation to terminate cationic polymerization.

The organic phase was analyzed by gas chromatography to determine percent monomer conversion (relative to an internal integration standard) and by gel permeation chromatography (using polystyrene standards) to determine polymer molecular weight and polydispersity index. In the case of N-vinylcarbazole, where a crosslinked gel formed, only the soluble components were analyzed. Results are summarized in Table 5.

TABLE 5

| Monomer | % Conversion | Cure Time | $M_n$ | PDI |
|---|---|---|---|---|
| Diphenyliodonium [TFPB] (Example 18) (catalyst) | | | | |
| cyclohexene oxide | 94 | 120 sec | 14,000 | 1.82 |
| N-vinyl carbazole | 99.4 | 30 sec | 75,000 (gel) | 5.78 |
| butyl vinyl ether | 99.0 | 10 sec | 8,800 | 2.97 |
| β-pinene | 99.3 | 15 sec | 2,400 | 2.1 |
| Diphenyliodonium [SbF$_6$] (Example C18) (catalyst) | | | | |
| cyclohexene oxide | 2.1 | — | — | — |
| N-vinyl carbazole | 75.7 | 60 sec | 11,300 | 2.92 |
| butyl vinyl ether | 0 | — | — | — |
| β-pinene | 0 | — | — | — |

(gel) means sample was partially gelled or crosslinked and therefore insoluble;
$M_n$ means number average molecular weight;
PDI means polydipersity index.
Where data are missing, no exotherm and no polymerization were observed.

The percent conversion and cure time data illustrate the improved photoactivity of the TFPB⁻ salt and the surprising effectiveness of this salt in the absence of added sensitizer. In the case of N-vinyl carbazole, the TFPB⁻ salt further provides significantly higher molecular weight and a higher level of crosslinking. Attempts to photoinitiate polymerization of N-vinylcarbazole with the free-radical photoinitiators, Irgacure™ 651 and CGI-784 (both commercially available from Ciba-Geigy), under similar conditions produced negligible monomer conversions indicating that the observed iodonium photoactivity was primarily cationic in nature.

Examples 19 and C19

These examples illustrate the advantageous properties of triarylsulfonium [TFPB] (Example 19), compared to triarylsulfonium SbF$_6$ (Comparative Example C19), in the photoinduced, nonsensitized polymerization of cationically sensitive monomers.

Triarylsulfonium [TFPB] was prepared according to the method of Example 4 using the same triarylsulfonium chloride precursor (from Fine Organics Ltd., supra) used to prepare the the SbF$_6^-$ salt. Comparative photo-polymerization trials were run on four different monomers (cyclohexene oxide, N-vinyl carbazole, butyl vinyl ether, and β-pinene) representing a broad variety of monomer types known to polymerize by cationic addition polymerization. Polymerizations were conducted in methylene chloride solution with equimolar concentrations of the triarylsulfonium [TFPB] and SbF$_6^-$ salts using the procedure described in Example 18 (above). Results are summarized in Table 6.

TABLE 6

| Monomer | % Conversion | Cure Time | $M_n$ | PDI |
|---|---|---|---|---|
| Triarylsulfonium [TFPB] (Example 19) (catalyst) | | | | |
| cyclohexene oxide | 99.8 | 5 sec | 11,900 | 1.85 |
| N-vinyl carbazole | 99.9 | 30 sec | 63,600 (gel) | 6.91 |
| butyl vinyl ether | 99.0 | 5 sec | 7,300 | 2.81 |
| β-pinene | 98.0 | 15 sec | 2,380 | 2.16 |
| Triarylsulfonium [SbF$_6$] (Example C19) (catalyst) | | | | |
| cyclohexene oxide | 99.9 | 10 sec | 13,000 | 1.89 |
| N-vinyl carbazole | 79.2 | 90 sec | 12,900 | 12.99 |
| butyl vinyl ether | 98.7 | 10 sec | 9,510 | 2.46 |
| β-pinene | 97.8 | 20 sec | 2,570 | 2.16 |

(gel) means sample was partially gelled or crosslinked and therefore insoluble;
$M_n$ means number average molecular weight;
PDI means polydipersity index.

The cure time data illustrate the photoactivity of the TFPB⁻ salt compared to the SbF$_6^-$ salt. In the case of N-vinyl carbazole, the TFPB⁻ salt further provides significantly higher monomer conversion, molecular weight and a higher level of crosslinking. Attempts to photoinitiate polymerization of N-vinylcarbazole with the free-radical photoinitiators, Irgacure™ 651 and CGI-784, under similar conditions produced negligible monomer conversions indicating that the observed sulfonium salt photoactivity was primarily cationic in nature.

Examples 20A–20B and C20

This example illustrates the solubility and photoreactivity of (aryl)$_3$S [TFPB] and PFTPB⁻ salts of the invention as compared to the corresponding SbF$_6^-$ salt, in the solventless curing of a difunctional vinyl ether monomer.

Triarylsulfonium [TFPB] and PFTPB⁻ salts were prepared according to the methods of Examples 4 and 9, respectively, using the same triarylsulfonium chloride precursor (from Fine Organics Ltd., supra) used to prepare the the SbF$_6^-$ salt. Comparative photo-polymerization trials were run in neat 1,4-cyclohexanedimethanol divinyl ether monomer (Rapi-cure™ CHVE Reactive Dilluent, GAF Chemicals Corp., Wayne, N.J.) using equal weight percent loadings (0.20 wt %) of the three (aryl)$_3$S$^+$ initiators according to the following procedure:

Three glass vials (2 dram) were loaded with separate 10 mg samples of the three (aryl)$_3$S$^+$ photoinitiator salts. Each of the photoinitiators were combined with 5 grams of CHVE monomer and and thoroughly mixed with a S/P™ Vortex Mixer (American Scientific Products) for 20 min at room temperature to promote dissolution. The (aryl)$_3$S [TFPB] and PFTPB⁻ salts dissolved completely. However, less than 50% of the SbF$_6^-$ salt dissolved under these conditions. Uncapped vials were lined up on the base of an inverted fluorescent lamp fixture equipped with two Sylvania F15T8/ BLB bulbs and irradiated. The elapsed irradiation time required to produce a vigorous polymerization exotherm (indicated by a sudden increase in the temperature of the samples, as noted by the appearance of heat induced convection currents, and concomitant rapid solidification of the sample) was noted in each case and recorded as a cure time. Recorded cure times are the average of duplicate trials. As summarized in Table 7, the cure times produced by the TFPB⁻ and PFTPB⁻ salts are shorter by a factor ranging from 1.8–4.5, respectively, than those produced by the SbF$_6^-$ salt, reflecting the greater photoactivity of the (aryl)$_3$S$^+$ salts of this invention.

TABLE 7

| Catalyst (Example) | Cure Time |
| --- | --- |
| (aryl)$_3$S [TFPB] (20A) | 10 sec |
| (aryl)$_3$S [PFTPB] (20B) | 25 sec |
| (aryl)$_3$S [SbF$_6$] (C20) | 45 sec |

Examples 21 and C21

These examples illustrate the properties of diphenyliodonium [PFTPB] (Example 21) as compared to diphenyliodonium [SbF$_6$] (Comparative Example C21), in the photoinduced, nonsensitized polymerization of cationically sensitive monomers.

Comparative photo-polymerization trials were run on three different monomers (cyclohexene oxide, butyl vinyl ether, and β-pinene) representing a broad variety of monomer types known to polymerize by cationic addition polymerization. Polymerizations were conducted in methylene chloride solution with equimolar concentrations of the diphenyiodonium PFTPB$^-$ and SbF$_6^-$ salts using the procedure described in Example 18. Results are summarized in Table 8.

TABLE 8

| Monomer | % Conversion | Cure Time | M$_n$ | PDI |
| --- | --- | --- | --- | --- |
| Diphenyliodonium [PFTPB] (Example 21) (catalyst) | | | | |
| cyclohexene oxide | 87.8 | 120 sec | 12,800 | 1.85 |
| butyl vinyl ether | 99.9 | 25 sec | 11,600 | 6.56 |
| β-pinene | 98.6 | 25 sec | 29,100 | 1.99 |
| Diphenyliodonium [SbF$_6$] (Example C21) (catalyst) | | | | |
| cyclohexene oxide | 0 | — | — | — |
| butyl vinyl ether | 0.3 | — | 57,700 | 2.23 |
| β-pinene | 0 | — | — | — |

M$_n$ means number average molecular weight; PDI means polydipersity index. Where no data are present, designated by (—), no exotherms were observed and therefore there was no observable polymerization of the monomer.

The percent conversion and cure time data illustrated the photoactivity of the PFTPB$^-$ salt and the effectiveness of this salt in the absence of added sensitizer. Comparison with the results in Example 18 further established the similarity in performance between the diphenyliodonium [PFTPB] and TFPB$^-$ salts.

Examples 22 and C22

This example illustrates the high photoactivity combined with thermal stability of epoxy compositions containing [(aryl)$_3$S] [TFPB] (Example 22) versus [(aryl)$_3$S] [SbF$_6$] (Comparative Example C22) photoinitiator.

Triarylsulfonium [TFPB] was prepared according to the method of Example 4 using the same triarylsulfonium chloride precursor (from Fine Organics Ltd.) used to prepare the the SbF$_6^-$ salt. Relative thermal stabilities were determined by DSC analysis of equimolar solutions of the (aryl)$_3$S$^+$ photoinitiators in neat ERL-4221 cycloaliphatic epoxy using a Seiko Instruments Inc. Model 220C DSC equipped with a Seiko Instruments Inc. Model PDC121 fiber optic light source for PDSC measurements.

Equimolar solutions of the initiator salts were prepared separately in the dark in small amber vials by combining 23 mg (aryl)$_3$S [TFPB] and 10 mg (aryl)$_3$S [SbF$_6$] with 1.5 grams of of ERL-4221. To ensure maximum dissolution of the photoinitiators in the epoxy monomer, the mixtures were heated at 35°–40° C for 2–4 hours with frequent mixing. A 4–5 mg aliquot of each solution was then transferred to an aluminum DSC pan, hermetically sealed and loaded, along with an empty reference pan, into the DSC chamber. DSC thermograms were recorded from 20°–450 ° C. while ramping the temperature at 10° C. per minute. The temperature at which the onset of thermally induced curing occurs in each case was determined by standard methods using the program software supplied with the Model 220C DSC, that is from the intersection of the baseline with a tangent drawn at the inflection point in the initial rise in the exotherm peak. For the (aryl)$_3$S [TFPB] salt solution the onset temperature was 202° C. compared to 177° C. for the (aryl)$_3$S [SbF$_6$] salt solution, representing a difference in thermal stability of almost 25° C.

To probe the photochemical activity of the (aryl)$_3$S [TFPB] salt after heating for an extended period of time at high temperatures in an epoxy monomer, the following experiment was conducted.

A 4.9 mg sample of the 4 day old, liquid solution of (aryl)$_3$S [TFPB] in ERL-4221 was transferred to an open aluminum DSC pan and loaded into the PDSC chamber along with an empty reference pan. The sample temperature was ramped up to 175° C. at 20° C. per minute and then held at this temperature for a period of 20 minutes while recording the thermogram. No curing exotherm was detected during this period. The sample was subsequently photolyzed at 175° C. in the PDSC chamber using the fiber optic light source powered by a 200 Watt mercury-xenon lamp and equipped with a Corning 7-59 bandpass filter and a 10% transmittance neutral density filter. With this configuration, the light striking the sample had a wavelength range of 280–500 nm and an intensity of 3.3 mW/cm$^2$. Immediately upon irradiation, a sharp and intense curing exotherm was produced with a measured energy of 378 J/g. These results illustrate the improved thermal stability and pot life of the (aryl)$_3$S [TFPB] salt in highly reactive epoxy monomers as well as the improved photochemical activity of this initiator following extended high temperature processing.

Example 23

This example illustrates the use of the compounds of this invention as photoinitiators for the preparation of cured silicone release coatings for pressure sensitive adhesives.

UV 9300 is a liquid silicone, viscosity of 250 centipoise, available from the General Electric Co., having an average molecular weight of approximately 9000 amu, with about 10 reactive epoxycyclohexyl ethyl substituents per chain (epoxy eq. wt. of 900). A solution of 1.0 gram of this silicone and 0.01 gram of (aryl)$_3$S [TFPB] (prepared as described in Example 4) was dissolved in 19 grams of isopropyl alcohol and coated on to a sheet of 1.5 mil unprimed polyester film using a No. 3 Meyer rod. The solvent was allowed to evaporate (providing a theoretical coating thickness of 0.3 micrometer of uncured silicone oil) before passing the coated film under a medium pressure mercury vapor lamp delivering an intensity of 50 mJ at 254 nm, and 125 mJ at 365 nm at a speed of 50 feet per minute. Immediately upon emerging from the light, the silicone was found to be cured to a clear, tack-free coating. This silicone coated film was then tested for its performance as a release film or liner for representative pressure sensitive adhesive tapes using a standard adhesion and readhesion test procedure.

This test measures the effectiveness of the silicone release composition after a period of heat aging. The aged release value is a quantitative measure of the force required to remove a flexible adhesive tape from a substrate coated with the test composition at a specific angle and rate of removal. In the following examples, this force is expressed in Newtons per decimeter (N/dm) from the following representative examples of flexible adhesive tapes:

| Tape A | tackified natural rubber coated on a 1.27 cm wide resin impregnated creped paper backing, and |
| Tape B | acrylate pressure-sensitive adhesive coated on 1.91 cm wide cellulose acetate backing. |

Aged release testing was conducted by laminating a 2.54 cm by 20.32 cm strip of the coated substrate (as prepared above) coated-side up to the stage of an Instrumentors, Inc. Slip/Peel Tester (model 3M90) with double-coated tape. A 1.27 cm by 15.24 cm strip of Tape A and 1.9 cm by 15.24 cm strip of Tape B pressure-sensitive adhesive (PSA) coated test tape was rolled down onto the laminate thus formed with a 1.82 kg rubber roller. The force required to remove this tape at 180° peel angle and 228.6 cm/minute after allowing the test tape to dwell in contact with the coated substrate for three days at 65° C. was then measured. The results of these tests are reported below. Re-adhesions after aging were also measured by adhering the freshly peeled tape to a clean glass plate and measuring the peel adhesion using the same Instrumentors Slip/Peel Tester indicated above, again peeling at 228.6 cm/min and at a 180° peel angle after allowing the test tape to dwell on the glass plate for 30 seconds. These measurements determined whether an unacceptably large drop in the adhesion value occurred due to undesirable transfer of significant quantities of unincorporated silicone in the release coating to the adhesive surface. Re-adhesions are reported as a percentage of the force required to remove the aged sample from a clean glass plate versus the force required to remove a control tape sample from a clean glass plate which has not been adhered to the release coating.

| Heat Aged Tape Test Results | |
| --- | --- |
| Tape A: | Release; Readhesion = 0.9 N/dm; 92% of Control |
| Tape B: | Release; Readhesion = 1.3 N/dm; 101% of Control |

Examples 24A–24B and C24

This example illustrates the enhanced solubility properties of diphenyliodonium [TFPB] and PFTPB⁻ salts (Examples 24A–24B) compared to diphenyliodonium [SbF$_6$] (Comparative Example C24) in solvents of low to medium polarity.

For relative solubility determinations, the solvents diethyl ether and methylene chloride were chosen because their polarities are similar to those of monomers used in cationic and free-radical polymerization. Solubilities were measured by taking known weights of each of the diphenyliodonium salts and diluting the samples with small portions of solvent, by thorough mixing between portions, until all the solid had dissolved. Solubilities are expressed as wt % of the iodonium salts in each solvent at room temperature and are summarized in Table 9.

TABLE 9

| Initiator (Example) | Diethyl Ether | Methylene Chloride |
| --- | --- | --- |
| Ph$_2$I [TFPB] (24A) | 46.8% | 51.0% |
| Ph$_2$I [PFTPB] (24B) | 22.5% | 39.8% |
| Ph$_2$I [SbF$_6$] (C24) | 0.23% | 0.3% |

The TFPB⁻ and PFTPB⁻ salts are comparable, however, both are a factor of 100 to 200 more soluble than the SbF$_6^-$ salt in each of the solvents.

Examples 25A–25C and C25

The purpose of this example is to demonstrate the use of TFPB⁻ salts of organometallic complex cations as photocatalysts for two part polyurethane curing.

A stock solution of 1.06 parts by weight trimethylolpropane, 26.6 parts Carbowax™ 400 (Union Carbide) and 13.2 parts hexane diisocyanate was prepared. Aliquots of 3 grams of stock solution were placed in glass vials and charged with catalyst according to Table 9 below. The samples were then placed on a hot plate with a surface temperature of approximately 50° C., and irradiated with a Kodak Carousel Projector at a distance of 3–4 inches. "Cure time" was the time required to cure the sample such that the resin did not flow when the vial was inverted. The TFPB⁻ salt was more soluble in the resin system than the background art photocatalyst containing the PF$_6^-$ counteranion. The TFPB⁻ salt did not require co-solvent to dissolve in the resin.

The data show the TFPB⁻ salts were effective photocatalysts for two-part polyurethane polymerization, and the TFPB⁻ salts had greater solubility and equal or shorter cure times than art known photocatalysts.

TABLE 10

| Photocatalyst (Example) | Catalyst Weight | Cure Time | Irradiated (?) |
| --- | --- | --- | --- |
| (mesitylene)(cyclopentadienyl) Fe [TFPB] (25A) | 16.9 mg in 0.1 g MEK | 4 mins | yes |
| (mesitylene)(cyclopentadienyl) Fe [TFPB] (25B) | 16.9 mg (no co-colvent) | 3 mins | yes |
| (mesitylene)(cyclopentadienyl) Fe [TFPB] (25C) | 16.9 mg (no co-colvent) | >9 mins | no |
| (mesitylene)(cyclopentadienyl) Fe [PF$_6$] (C25) | 7.8 mg in 0.1 g MEK (equal molar basis as TFPB⁻ salt) | 4 mins | yes |

Examples 26 and C26A–C26B

This example illustrates the properties of (benzene)Mn(CO)$_3$ [TFPB] in cyanate ester curing.

Three samples of L-10 resin were prepared as follows:

| Example | Mixture components |
|---------|---------------------|
| C26A | L-10 alone |
| C26B | L-10 plus 0.24 weight percent $(C_6H_6)Mn(CO)_3$ $[PF_6]$ |
| 26 | L-10 plus 0.21 weight percent $(C_6H_6)Mn(CO)_3$ [TFPB]. |

The $(C_6H_6)Mn(CO)_3$ [TFPB] catalyst readily dissolved in the cyanate ester in Example 26, whereas $(C_6H_6)Mn(CO)_3$ $[PF_6]$ did not completely dissolve in the cyanate ester in Example C26B.

Small aliquots from Examples C26A–C26B and 26, 7–10 milligrams, were sealed in aluminum pans and differential scanning calorimetry (DSC) was carried out at a 10° C./minute heating rate. Fresh 7–10 milligram aliquots from all the Examples were placed in aluminum pans and were irradiated for 5 minutes with the light from two 15 watt F15T8-BLB Blacklight bulbs (General Electric), which were ½ inch distant from the DSC pans. The pans were then sealed and DSC scans were run as above. The results are summarized in Table 11.

TABLE 11

| Entry No. | Example | Irradiated? | DSC Peak (°C.) | Energy (J/g) |
|-----------|---------|-------------|----------------|--------------|
| 1 | C26A | no | 256.2 | 711 |
| 2 | C26A | yes | 261.0 | 683 |
| 3 | C26B | no | 147.6 | 78 |
|   |      |     | 250.3 | 600 |
| 4 | C26B | yes | 170.3 | 670 |
| 5 | 26 | no | 182.8 | 728 |
| 6 | 26 | yes | 177.7 | 700 |

Entries 1 and 2 show L-10 cured at about 260° C. in the absence of catalyst with the release of approximately 700 J/g and its cure was not activated by irradiation. Entry 3 shows that $(C_6H_6)Mn(CO)_3$ $[PF_6]$ was not a particularly effective thermal catalyst for L-10 cure in that only a very small low temperature exotherm was detected with the remainder of the cure resembling that of uncatalyzed L-10. Entry 4 shows that $(C_6H_6)Mn(CO)_3$ $[PF_6]$ was an effective catalyst for L-10 cure after photoactivation with all of the cure occurring at about 100° C. below that of uncatalyzed L-10. Entry 5 shows that $(C_6H_6)Mn(CO)_3$ [TFPB] was an effective thermal catalyst for L-10 cure and the lack of a high temperature exotherm shows $(C_6H_6)Mn(CO)_3$ [TFPB] was a better thermal catalyst than $(C_6H_6)Mn(CO)_3$ $[PF_6]$ for L-10 cure. Entry 6 shows a small beneficial effect of photoactivation of $(C_6H_6)Mn(CO)_3$ [TFPB] in L-10 cure. This example thus shows the improved properties of $(C_6H_6)Mn(CO)_3$ [TFPB] over $(C_6H_6)Mn(CO)_3$ $[PF_6]$ as a thermal curative for cyanate ester resins.

Examples 27 and C27

This example illustrates the advantage of [N,N-diethylanilinium] [TFPB] (Example 27) as a latent curing agent for epoxy/polyol formulations over [N,N-diethylanilinium] $[SbF_6]$ (Comparative Example C27).

Mixtures of DGEBA epoxy and ethylene oxide chain-extended bisphenol A type polyols (SYN FAC 8024, Milliken) with a ratio of epoxide:hydroxide of 1:0.4 were cured using 1 wt % (based on total weight of monomers) of catalyst salt. The catalyst salt (0.020 g) was dissolved/suspended in 0.588 g of the polyol SYN FAC 8024 (epoxy eq. wt.=180). This mixture was added to 1.412 g of DGEBA. A small aliquot (10–20 mg) was removed and placed in an aluminum pan and differential scanning calorimetry (DSC) was carried out on a Perkin Elmer DSC7 with a heating rate of 10° C./min. The results are summarized in Table 12.

TABLE 12

| Catalyst Salt (Example) | $T_{peak}$ (°C.) | $T_{onset}$ (°C.) | Exotherm (J/g) |
|-------------------------|------------------|-------------------|-----------------|
| N,N-diethylanilinium $[SbF_6]$ (C27) | | | |
| Peak 1 | 69 | 48 | −20.8 |
| Peak 2 | 151 | 127 | −16.3 |
| Peak 3 | 231 | 192 | −86.6 |
| N,N-diethylanilinium [TFPB] (27) | 155 | 118 | −415.5 |

The two salts, differing only in the counterion show different cure profiles by DSC. The DSC thermograms differ by the number of peaks observed, the temperature of the maximum peak, and the total exotherm energy. The $SbF_6^-$ salt DSC thermogram showed three unsymmetrical small peaks spanning a wide spread of temperatures. These multiple peaks implied that more than one curing pathway may be in operation. The first peak (onset temperature of 48° C.) extended to room temperature, and therefore curing proceeded at room temperature. Samples of epoxy/polyol/[N,N-diethylanilinium] $[SbF_6]$ gelled in less than 30 minutes at room temperature. The short pot-life of this material prohibited its use as a latent curing agent. While curing began at room temperature, the low total exotherm energy (123.7 J/g) demonstrated that complete curing had not occurred even at relatively high temperatures.

Mixtures of epoxy/polyol/[N,N-diethylanilinium] [TFPB] demonstrated room temperature latency, showing no tendency to gel at room temperature even after several weeks. The large exotherm indicated the greater ability of this salt to provide complete curing of the epoxy/polyol mixture. The data illustrates the TFPB− counterion allowed better control of the cure, more complete curing and superior latency.

Examples 28A–28B and C28A–C28B

This example demonstrates how the thermally induced curing of epoxy/polyol mixtures correlates with the $pK_a$ of the TFPB− salt, but is relatively independent of the isomeric structure of the cation. The example further demonstrates the improved activity of TFPB− salts compared to $SbF_6^-$ salts in catalyzing the curing of epoxy/polyol mixtures.

Mixtures of DGEBA and polyol (SYN FAC 8024, Milliken) with a ratio of epoxide:hydroxide of 1:0.4 were cured using 1 wt % (based on the total weight of the monomers) of catalyst salt. The catalyst salt (0.020 g) was dissolved/suspended in 0.588 g of the polyol. This mixture was then added to 1.412 g of DGEBA. A small aliquot (10–20 mg) was removed and placed in an aluminum pan and DSC was carried out at a heating rate of 10° C./minute. The results are summarized in Tables 13 and 14.

TABLE 13

| Salt[a] | $pK_a$[b] | $T_{peak}$ (°C.) | $T_{onset}$ (°C.) |
|---------|-----------|------------------|-------------------|
| pyrrolium | −0.27 | 94 | 83 |
| $Ph_2NH_2$ | 0.9 | 98 | 68 |
| p-nitroanilinium | 1.02 | 105 | 86 |
| [o-$H_3N(C_6H_4)CO_2Me$] | 2.23 | 88 | 56 |

TABLE 13-continued

| Salt[a] | pK$_a$[b] | T$_{peak}$ (°C.) | T$_{onset}$ (°C.) |
|---|---|---|---|
| [p-H$_3$N(C$_6$H$_4$)CO$_2$Me] | 2.38 | 103 | 72 |
| N,N-dimethylanilinium | 5.06 | 134 | 103 |
| p-toluidinium | 5.12 | 101 | 89 |
| N,N-diethylanilinium | 6.56 | 153 | 126 |
| imidazolium | 7.03 | no cure | no cure |
| Bu$_3$NH | 10.89 | no cure | no cure |

[a]All salts have TFPB$^-$ counterions
[b]Literature values, from Alber et al., Ionization Constants of Acids and Bases, pg. 140–145 (1962), John Wiley & Sons.

Table 13 shows that there is a good correlation between the acidity of the TFPB$^-$ salts and the temperature at which they will cure an epoxy/polyol mixture. Because the pK$_a$ values were determined in aqueous solutions, some variance was expected. However, the general trend of increasing acidity giving lower cure temperatures generally holds.

The pK$_a$/cure temperature relationship holds when TFPB$^-$ salts of similar pK$_a$ but different isomeric structures are compared. The o- and p-ammonium salts of the methyl ester of benzoic acid have similiar pK$_a$ values. Table 14 summarized below shows the isomeric TFPB$^-$ salts (Examples 28A–28B) behave very similarly, with the slightly more acidic ortho- salt curing at slightly lower temperature. The corresponding pair of SbF$_6^-$ salts (Comparative Examples C28A–C28B) on the other hand give significantly different DSC thermograms. The thermogram of the ortho- SbF$_6^-$ resembled that of the TFPB$^-$ salt, however, the para- SbF$_6^-$ gave two distinct peaks in the DSC thermogram. Furthermore, the magnitude of the curing exotherm was much higher for the TFPB$^-$ salts than for the corresponding SbF$_6^-$ salts, indicating more complete curing with the TFPB$^-$ salts. Thus, the TFPB$^-$ salts induce more complete curing and provide improved correllation between pK$_a$ and thermal cure temperature when compared to the corresponding SbF$^{6-}$ salts.

TABLE 14

| Catalyst Salt (Example) | T$_{peak}$ (°C.) | T$_{onset}$ (°C.) | Exotherm (J/g) |
|---|---|---|---|
| [p-H$_3$N(C$_6$H$_4$)CO$_2$Me] [TFPB] (28A) | 103 | 72 | −304.0 |
| [o-H$_3$N(C$_6$H$_4$)CO$_2$Me] [TFPB] (28B) | 88 | 56 | −319.7 |
| [p-H$_3$N(C$_6$H$_4$)CO$_2$Me] [SbF$_6$] (C28A) | | | |
| Peak 1 | 93 | 63 | −190.9 |
| Peak 2 | 177 | 151 | −49.9 |
| [o-H$_3$N(C$_6$H$_4$)CO$_2$Me] [SbF$_6$] (C28B) | 88 | 63 | −191.3 |

Examples 29A–29D and C29A–C29B

This example illustrates the thermal activity of protic, nitrogen-centered onium TFPB$^-$ salts for the polymerization of a cycloaliphatic epoxy monomer.

Each of the nitrogen-centered onium TFPB$^-$ salts in Table 15 were transferred to 2 dram glass vials in the amounts given. Each sample was combined with 2 mL of cyclohexene oxide and stirred to ensure complete dissolution. The uncapped vials containing the solutions which did not polymerize at room temperature were immediately placed on a hot plate set to a surface temperature of 115° C. for a total time of 30 minutes. If the solutions showed no evidence of polymerization after 30 min at 115° C., the temperature was quickly ramped to about 130° C. In each case, the time required to initiate polymerization of the cyclohexene oxide at a given temperature was recorded. The onset of polymerization was indicated by a sudden reaction exotherm and a simultaneous increase in sample viscosity. Results are summarized in Table 15. The activities displayed by tetra-n-butylammonium [TFPB] and tri-n-butyl amine are included for comparison.

TABLE 15

| Example | Initiator (Wt) | Cure Temperature/ Cure Time |
|---|---|---|
| 29A | N,N-dimethylanilinium [TFPB] (13 mg) | 25° C./instantaneous |
| 29B | 2,6-di-t-butyl-4-methylpyridinium [TFPB] (10 mg) | 25° C./instantaneous |
| 29C | tri-n-butylammonium [TFPB] (10 mg) | 115° C./5 min |
| 29D | triethylammonium [TFPB] (7 mg) | 130° C./1 min |
| C29A | tetra-n-butylammonium [TFPB] (6 mg) | No curing observed up to 130° C. |
| C29B | tri-n-butylamine ~15 mg) | No curing observed up to 130° C. |

The tabulated data indicate that only those nitrogen centered onium TFPB$^-$ salts containing at least one acidic H—N$^+$ group were active thermal initiators for cyclohexene oxide polymerization under these reaction conditions. Furthermore, the relative activities of these salts, as reflected by their cure temperatures and cure times, correlated roughly with the relative acidities of the onium portion; that is, the most acidic onium salts displayed the greatest activity. Neutral amines, like tri-n-butylamine, showed no activity.

Example 30

This example illustrates the thermally induced curing activity of Na [TFPB] in a cycloaliphatic epoxy monomer.

Two 3 dram vials were each charged with 3 mL of cyclohexene oxide and about 300 mg of activated 3A molecular sieves (Aldrich Chemical Company). To one vial was added 58 mg Na [TFPB]·(3 H$_2$O), which dissolved readily upon mixing. The second vial contained no initiator and served as the control. Both vials were placed on a hot plate and gradually heated to 200° C. At about 180° C., the sample containing the Na [TFPB] salt began to boil gently and gradually became viscous over a period of 45 minutes indicating that slow polymerization was occuring. No evidence of polymerization was observed in the control sample. Upon cooling to room temperature, the partially polymerized sample was a viscous syrup, whereas the control showed no significant change in viscosity. No evidence of further polymerization was observed in either case upon standing at room temperature for a period of 3 days. However, heating of the Example containing Na [TFPB] close to the boiling point of the monomer for about 1 minute followed by cooling to room temperature produced a significant increase in viscosity, indicating that the initiator was still readily reactivated by heat. $^1$H NMR analysis of the cured sample containing Na [TFPB] indicated that the conversion of cyclohexene oxide to polymer was incomplete with 28% unreacted monomer remaining. GPC analysis showed that the polymer produced had a molecular weight ($M_n$) of 3,800 amu, which is relatively high (by a factor of 3-4) compared to poly(cyclohexene oxide) produced with nitrogen-centered onium and organometallic TFPB$^-$ salts.

Example 31

This example illustrates the thermally induced curing activity of Li [TFPB] in a cycloaliphatic epoxy.

Three 3 dram vials were each charged with the following reagents:

| Vial #1: | 2 mL cyclohexene oxide, 300 mg 3A molecular sieves (Control); |
|---|---|
| Vial #2: | 2 mL cyclohexene oxide, 35 mg Li [TFPB]-(2 H$_2$O); |
| Vial #3: | 2 mL cyclohexene oxide, 35 mg Li [TFPB]-(2 H$_2$O), 300 mg 3A molecular sieves. |

In each case the lithium salt dissolved completely in the monomer. The vials were sealed with polyethylene caps pierced with 18 gauge syringe needles to relieve pressure during heating or polymerization. Each of the vials was place on a hot plate heated to 100° C. (surface temperature). The surface temperature of the hot plate was gradually ramped to 210° C. at approximately 4 degrees per minute while the samples were visually inspected for evidence of polymerization. At a surface temperature of 136° C. the sample in vial #2 began polymerizing as evidenced from a significant increase in viscosity. Similar polymerization of the sample in vial #3 was observed at 158° C. In both cases, polymerization was slow and controlled and did not exhibit the large and rapid reaction exotherm usually observed with cyclohexene oxide. No polymerization of the sample in vial #1 (control) was observed up to 210° C., indicating that the polymerization activity observed in the other samples was thermally initiated by the Li [TFPB] present. Comparison with the results obtained with Na [TFPB] in the same monomer (Example 30) indicates that the lithium salt is a more active thermal initiator than the sodium salt. Polymerization of cyclohexene oxide with Li [TFPB] in the presence of 3A molecular sieves at 150°-160° ° C. for approximately one hour according to the above described procedure was shown by $^1$H NMR to have proceeded to 82% conversion. By GPC analysis, the number average molecular weight of the poly(cyclohexene oxide) produced was determined to be 2,913 amu relative to polystyrene standards.

Example 32

This example illustrates the utility of (aryl)$_3$S [B(n-butyl)(C$_6$F$_5$)$_3$] in the curing of a difunctional vinyl ether monomer.

(Aryl)$_3$S [B(n-butyl)(C$_6$F$_5$)$_3$] was prepared according to the method described in Example 7 using the triarylsulfonium chloride mixture from Fine Organic Ltd. Photopolymerizations were conducted using 1,4-cyclohexanedimethanol divinyl ether monomer (Rapi-cure™ CHVE Reactive Diluent, GAF Chemicals) dissolved in a mixture of methyl ethyl ketone (MEK) and methylene chloride solvents using 0.2 wt % of the photoinitiator (relative to monomer) according to the following procedure:

A glass 2 dram vial was loaded with 10 mg of (aryl)$_3$S [B(n-butyl)(C$_6$F$_5$)$_3$]. The photoinitiator was predissolved in 30 mg MEK, then 5.00 g CHVE monomer and I mL methylene chloride was added and the mixture thoroughly mixed with a S/P™ Vortex Mixer (American Scientific Products) for 5 minutes at room temperature to ensure complete dissolution of the initiator. A 0.5 mL aliquot of this solution was transferred to a clear 2 dram vial that was in turn positioned on the base of an inverted fluorescent lamp fixture equipped with two Sylvania F15T8/BLB bulbs and irradiated at room temperature. The elasped irradiation time required to produce a vigorous polymerization exotherm (indicated by a sudden increase in the temperature of the samples and concomitant rapid boiling of the solution) was 21 seconds (average of 5 determinations). The cured resin was a hard, brittle, light orange solid.

Examples 33 and C33

A photolysis test was carried out (as described in Examples 17A-17B) to compare the efficiency of diphenyliodonium [TFPB] and diphenyliodonium [SbF$_6$] as initiators of cationic polymerization.

Example 33 contained 0.010 g of diphenyliodonium [TFPB], 0.005 g KB-1 and 2.03 g of cyclohexene oxide. Comparative example C33 contained 0.005 g of diphenyliodonium [SbF$_6$] (to make it equimolar with the TFPB$^-$ salt), 0.005 g KB-1 and 2.01 g of cyclohexene oxide. The examples were placed in glass vials and irradiated for 10 sec with two 15 watt Sylvania F15T8/BLB bulbs at a distance of 1 cm. Example 33 polymerized exothermically, boiling out of the vial while Example C33 did not appear to react. NMR was used to determine the percent conversion of the cyclohexene oxide monomer to polymer. For Example 33, the conversion was >97%, whereas for Example C33 the conversion was 0%, that is, no polymer was detected.

This example demonstrated the increased efficiency of the TFPB$^-$ salt over the SbF$_6^-$ salt as an initiator of cationic polymerization.

Examples 34 and C34

A photo-DSC test was carried out (as described in Examples 17A-17B) to compare the efficiency of diphenyliodonium [TFPB] and diphenyliodonium [SbF$_6$] as initiators of cationic polymerization.

Example 34 contained 0.020 g of diphenyliodonium [TFPB], 0.01 g KB-1 and 1.00 g of ERL-4221. Comparative example C34 contained 0.01 g of diphenyliodonium [SbF$_6$] (to make it equimolar with the TFPB$^-$ salt), 0.01 g KB-1 and 1.00 g of ERL-4221. Photo-DSC measurements were made on 14-16 mg samples at 60° C. Corrections were made for the heat absorbed by the sample and for any difference in light absorption of the two sides of the sample cell. The energy produced from the polymerization of the epoxy was determined at various exposure times. The results are summarized in Table 16.

TABLE 16

| Exposure | Energy in J/g | |
|---|---|---|
| Time (minutes) | Example 34 | Comparative Example C34 |
| 4 | 440 | 371 |
| 2 | 415 | 342 |
| 1 | 413 | 322 |
| 0.5 | 399 | 291 |
| 0.25 | 284 | 210 |
| 0.12 | 162 | 129 |
| 0.06 | 98 | 60 |
| 0.03 | 49 | 17 |

The results in Table 16 show that for all exposure times, the TFPB⁻ salt has a higher exotherm energy than the $SbF_6^-$ salt. Because the energy measured in this test is proportional to the amount of epoxy that is polymerized, the TFPB⁻ salt is a more efficient initiator of cationic polymerization than the $SbF_6^-$ salt.

Examples 35 and C35

A Photo-DSC (PDSC) test was carried out (as described in Examples 17A–17B) to compare the efficiency of diphenyliodonium [TFPB] and diphenyliodonium [$SbF_6$] as initiators of cationic polymerization. Example 35 contained 0.020 g of diphenyliodonium [TFPB] and 1.00 g of ERL-4299. Comparative example C35 contained 0.01 g of diphenyliodonium [$SbF_6$] (to make it equimolar with the TFPB⁻ salt) and 1.00 g of ERL-4299. PhotoDSC measurements were made on 9–12 mg samples at a constant exposure time of 5 minutes. Corrections were made for the heat absorbed by the sample and for any difference in light absorption of the two sides of the sample cell. The energy produced from the polymerization of the epoxy and the time to reach the peak maximum of the exotherm were determined at various temperatures. The results are summarized in Table 17.

TABLE 17

| Temperature (°C.) | PDSC Exotherm (J/g) | | Time to Reach Peak Maximum (seconds) | |
|---|---|---|---|---|
| | Ex 35 | Ex C35 | Ex 35 | Ex C35 |
| 40.5 | 32 | 33 | 28 | 88 |
| 60.8 | 94 | 61 | 22 | 59 |
| 81.2 | 232 | 217 | 20 | 51 |
| 101.5 | 342 | 310 | 32 | 39 |

The results in Table 17 show that the TFPB⁻ salt had a slightly higher exotherm energy when compared to the $SbF_6^-$ salt. The time to reach the peak maximum was always shorter for the TFPB⁻ salt, often by a factor of two or more. This demonstrated that the TFPB⁻ salt was a more active compound, reacted more rapidly and produced faster cures than the $SbF_6^-$ salt.

Examples 36 and C36

A PDSC test was carried out (as described in Examples 17A–17B) to compare the efficiency of diphenyliodonium [TFPB] and diphenyliodonium [$SbF_6$] as initiators of cationic polymerization. Example 36 contained 0.020 g of diphenyliodonium [TFPB] and 1.00 g of ERL-4299. Comparative example C36 contained 0.01 g of diphenyliodonium [$SbF_6$] (to make it equimolar with the TFPB⁻ salt) and 1.00 g of ERL-4299. Photo-DSC measurements were made on 9–12 mg samples at a constant temperature of 80° C. Corrections were made for the heat absorbed by the sample and for any difference in light absorption of the two sides of the sample cell. The energy produced from the polymerization of the epoxy was determined at various exposure times. The results are presented in Table 18.

TABLE 18

| Exposure Time (minutes) | Example 36 Exotherm (J/g) | Example C36 Exotherm (J/g) |
|---|---|---|
| 1 | 87 | 52 |
| 0.5 | 59 | 18 |
| 0.1 | 32 | 0.2 |

TABLE 18-continued

| Exposure Time (minutes) | Example 36 Exotherm (J/g) | Example C36 Exotherm (J/g) |
|---|---|---|
| 0.05 | 8 | 0.2 |
| 0.02 | 1 | 0 |

The data in Table 18 show that the TFPB⁻ salt produced a larger exotherm over the range of exposure times when compared to the $SbF_6^-$ salt. The difference became large at the shorter exposure times when the TFPB⁻ salt out-performed the $SbF_6^-$ by a factor of three or more. Since the exotherm energy was related to the amount of cure, the TFPB⁻ was more efficient than the $SbF_6^-$ salt.

Example 37

The bis(cyclopentadienyl)iron [TFPB] salt was prepared by dissolving 0.99 g of ferrocene and 0.29 g of benzoquinone in 150 ml of ethanol. The solution was purged for about 15 minutes with nitrogen. While stirring and purging, 0.19 g of concentrated HCl was added to the ethanol solution. An immediate reaction took place and a deep blue color formed. A solution of 5.0 g Na [TFPB].(3H₂O) in 300 ml water and 50 ml ethanol was prepared and purged with nitrogen. The ethanol solution of the ferrocenium chloride salt was added to the Na [TFPB] solution. A blue precipitate formed and was filtered off, washed with ethanol and dried in a vacuum oven. The yield was 3.90 gram of ferrocenium [TFPB].

Example 38

The ferrocenium [TFPB] salt prepared in Example 37 was used to prepare thermally curable epoxy/polyol compositions for DSC tests (as described in Examples 16A–16B). An epoxy/polyol mixture was prepared from DGEBA and 1,4-butanediol at an epoxy/hydroxy ratio of 1:0.4 using 188 as the epoxy equivalent weight for DGEBA. Thermally curable compositions were prepared from 5 g of the DGEBA/1,4-butanediol mixture and 0.2, 0.1, 0.05 0.025 and 0.012 g of ferrocenium [TFPB]. Sufficient y-butyrolactone was used to dissolve the catalyst, approximately 0.1 g or less. DSC runs were made on samples and the exotherm energy and exotherm peak temperature were recorded. The results are presented in Table 19.

TABLE 19

| Weight % of TFPB⁻ salt | Peak Maximum (°C.) | Exotherm Energy (J/g) |
|---|---|---|
| 4.0 | 102 | 387 |
| 2.0 | 102 | 395 |
| 1.0 | 115 | 401 |
| 0.5 | 118 | 411 |
| 0.25 | 133 | 390 |

The results in Table 19 demonstrated that the ferrocenium [TFPB] salt was an efficient thermal initiator for cationic polymerization under a wide range of concentrations.

Example 39

A sample was prepared from 0.05 g diphenyliodonium [TFPB], 0.1 gram y-butyrolactone and 5.0 g of SR295. A PDSC test was run (as described in Examples 17A–17B) at 51° C. with an exposure time of 5 minutes to measure the efficiency of the TFPB⁻ salt as a photoinitiator of free radical polymerization. The run produced a sharp exotherm of 167 J/g, indicating that the TFPB⁻ salt is active as a photoinitiator of free radical polymerization.

Various modifications and alterations of this invention will become apparent to those skilled in the art without departing from the scope and principles of this invention, and it should be understood that this invention is not to be unduly limited to the illustrative embodiments set forth herein above. All publications and patents are herein incorporated by reference to the same extent as if each individual publication or patent was specifically and individually indicated to be incorporated by reference.

What is claimed:

1. A polymerizable composition comprising:

(a) at least one of a cationic addition polymerizable monomer; a free-radically polymerizable ethylenically-unsaturated monomer; a catalyzed step-growth monomer; or mixtures thereof and, (b) at least one of the salts of nonnucleophilic anions wherein the cationic portion of the salt is selected from the group consisting of:

(1) mono- or polyvalent metal cations having a valence of 1–5 selected from the group consisting of metals of Groups IA and IIA and those of the lanthanide and actinide serires of the Periodic Table of Elements (CAS version);

(2) organic onium cations selected from the group consisting of aliphatic or aromatic Group IVA–VIIA (CAS version) centered onium salts, and protonated aliphatic, aromatic or heterocyclic amines; or (3) organometallic complex cations essentially free of metal hydride or metal alkyl functionality and has the formula:

$$[(L^1)(L^2)M]^{+q}$$

wherein

M represents a metal selected from the group consisting of Cr, Mo, W, Mn, Re, Fe, Ru, Os, Co, Rh, Ir, Pd, Pt and Ni;

$L^1$ represents 1 or 2 cyclic, polyunsaturated ligands that can be the same or different ligands selected from the group consisting of substituted and unsubstituted cyclopentadienyl, cyclohexyldienyl, and cycloheptatrienyl, cyclohetatriene, cyclooctatetraene, heterocyclic compounds and aromatic compounds selected from substituted and unsubstituted benzene compounds and compounds having 2 to 4 fused rings, each capable of contributing 3 to 8 electrons to the valence shell of M;

$L^2$ represents none, or 1 to 3 nonanionic ligands contributing an even number of electrons that can be the same or different ligands selected from the group of carbon monoxide, ketones, olefins, ethers, nitrosonium, phosphines, phosphites, and related derivatives of arsenic and antimony organonitriles, amines, alkynes, isonitriles, dinitrogen, with the proviso that the total electronic charge contributed to M results in a net residual positive charge of q to the complex;

q is an integer having a value of 1 or 2, the residual charge of the complex cation;

the anionic portion of the salts has the formula:

$$[(M')^{m+}Q_1Q_2\ldots Q_n]^{d-}$$

wherein:

M' is a metal or metalloid selected from the groups subtended by Groups IVB to VB of the Periodic Table of the Elements (CAS version);

$Q_1$ to $Q_n$ are selected, each independently from the group consisting of halide radicales, dialkylamido radicals, hydroxide, alkoxide and aryloxide radicals, hydrocarbylmercaptide and -carboxylate radicals, hydrocarbyl and substituted hydrocarbyl radicals, and organometalloid radicals, where at least one of $Q_1$ to $Q_n$ is a nalogen-substituted aromatic hydrocarbyl radical, but not more than $(n-1)$ of $Q_1$ to $Q_n$ may be halide radical, with the remaining $Q_1$ to $Q_n$ being selected from the foregoing radicals;

m is an integer from 1 to 6;

n is an integer from 2 to 7; and $(n-m)=d$.

2. The polymerizable composition according to claim 1 wherein the nonnucleophilic anion has the formula:

$$[BArQ_2Q_3Q_4]^-$$

wherein:

n is 4

M' is boron (B) in a valence state of 3;

$Q_1$ is Ar, a halogen substituted aromatic hydrocarbon radical containing from about 6 to about 30 carbon atoms and optionally, linked to one or more Q groups through one or more stable bridging groups, wherein the bridging groups include a single bond, double bond —$((CH_2)_n)$—, where n is 1 to 4; —$((CF_2)_m)$—, where m is 1 to 4; —$(CH_2)$—; $(R)_2Si=$; $(R)_2Sn=$; $(R)_2Ge=$; $(R)_2C=$; O; S; Se; =CO; =$SO_2$; RN=; or RP=; where R is substituted aryl, unsubstituted aryl, substituted alkyl or unsubstituted alkyl hydrocarbyl group; and $Q_2$, $Q_3$ and $Q_4$ are as defined in claim 1.

3. The polymerizable composition according to claim 2 wherein the onium cations of the initiator salt are selected from the group consisting of diazonium, sulfoxonium, diaryliodonium, and triarylsulfonium.

4. The polymerizable composition according to claim 2 wherein the anionic portion contains a multiplicity of perfluorinated or $CF_3$-substituted aromatic hydrocarbon rings bound to a boron center and at least one nonpolar monomer selected from epoxy-functional silicones, multifunctional unsaturated hydrocarbons, unsaturated or epoxidized triglycerides.

5. The polymerizable composition according to claim 4 wherein the anion is $[3,5-(CF_3)_2C_6H_3]_4B^-$ or $(C_6F_5)_4B^-$.

6. The polymizable composition according to claim 2 wherein the onium and cationic organometallic photoinitiator salts have at least one of $[3,5-(CF_3)_2C_6H_3]_4B^-$ or $(C_6F_5)_4B^-$ anionic portion and at least one cationically polymerizable monomer.

7. The polymerizable composition according to claim 2 wherein the initiator is a salt or salt.

8. The polymerizable composition according to claim 7 wherein the boron-centered anion is $[[3,5-(CF_3)_2C_6H_3]_4B]$ or $[(C_6F_5)_4 B]$.

9. The polymerizable composition according to claim 2 wherein the initiator salt a nonnucleophilic anionic portion and a cationic portion that is a monovalent or polyvalent metal cation selected from the group consisting of metals of Group IA and IIA and those of the lanthanide and actinide series of the Periodic Table of the Elements and at least one cationically polymerizable monomer selected from epoxy monomers or vinyl ether monomers.

10. The polymerizable composition according to claim 9 wherein the cationic portion is $Na^+$ or $Li^+$ and anionic portion is $[3,5-(CF_3)_2C_6H_3]_4B^-$ or $(C_6F_5)_4B^-$.

11. The polymerizable composition according to claim 2 wherein the organometallic cation of the initiator salt has the formula:

$$[(L^1)(L^2)M]^{+q}$$

wherein

M represents a metal selected from the group consisting of Cr, Mn, Fe, Co, Ni, and Pd;

$L^1$ represents 1 or 2 cyclic, polyunsaturated ligands that can be the same or different ligand selected from the group consisting of substituted and unsubstituted cyclopentadienyl, and aromatic compounds selected from substituted or unsubstituted benzene compounds and compounds having 2 to 4 fused rings;

$L^2$ represents none, or 1 to 3 nonanionic ligands contributing an even number of electrons that can be the same or different ligand selected from the group of carbon monoxide, ketones, olefins, ethers, nitrosonium, phosphines, phosphites, and related derivatives of arsenic and antimony organonitriles, amines, alkynes, isonitriles, dinitrogen, with the proviso that the total electronic charge contributed to M results in a net residual positive charge of q to the complex;

q is an integer having a value of 1 or 2, the residual charge of the complex cation.

12. The polymerizable compositions according to claim 11 wherein the organometallic cations are selected from the group consisting of (cyclopentadienyl)(arene)iron, $(arene)Mn(CO)_2L^2$, $(arene)_2iron$, $(cyclopentadienyl)iron(CO)_2L^2$, $(methylcyclopentadienyl)Mn(CO)_2(NO)$, $(arene)_2Cr$, and $(cyclopentadienyl)_2iron$.

13. The polymerizable composition according to claim 1 wherein the cationically polymerizable monomer is selected from the group consisting of epoxies, cyclic ethers, vinyl ethers, vinylamines, unsaturated hydrocarbons, lactones and other cyclic esters, lactams, cyclic carbonates, cyclic acetals, aldehydes, cyclic amines, cyclic sulfides, cyclosiloxanes, and cyclotriphosphazenes.

14. The polymerizable composition according to claim 1 wherein the free radically polymerizable ethylenically-unsaturated monomer is selected from the group consisting of acrylates and methacrylates, acrylamides, methacrylamides, and other vinyl compounds.

15. The polymerizable composition according to claim 1 wherein catalyzed step-growth polymerizable monomers selected from the group consisting of a multifunctional isocyanate in combination with a multifunctional alcohol; a mutifunctional epoxy in combination with a multifunctional alcohol; and multifunctional cyanate esters.

* * * * *

UNITED STATES PATENT AND TRADEMARK OFFICE
CERTIFICATE OF CORRECTION

PATENT NO.: 5,514,728

DATED: May 7, 1996

INVENTOR(S): Lamanna et al.

It is certified that error appears in the above-identified patent and that said Letters Patent is hereby corrected as shown below:

Col. 8, line 46, Delete "$Mg[(B[3,5-(CF_3)_2C_6H_4]_4)_2]$" and insert --$Mg[(B[3,5-(CF_3)_2C_6H_3]_4)_2]$,--.
Col. 13, line 4, Delete "PF6" and insert --$PF_6$--
Col. 13, line 37, Delete "$[3,5-(CF^3)_2C_6H_3]_4B^-$" and insert --$[3,5-(CF_3)_2C_6H_3]_4B^-$--
Col. 20, line 15, Delete "Edenmeyer" and insert --Erlenmeyer--
Col. 20, line 15, Delete "0.41 4" and insert --0.414--
Col. 31, line 62, Delete "hisphenol" and insert --bisphenol--
Col. 34, Table 15, last example, Insert --(-- before ~

Signed and Sealed this

Fourth Day of February, 1997

Attest:

BRUCE LEHMAN

Attesting Officer

Commissioner of Patents and Trademarks